(12) United States Patent
Zhao et al.

(10) Patent No.: US 10,376,336 B2
(45) Date of Patent: *Aug. 13, 2019

(54) TOUCHLESS ADVANCED IMAGE PROCESSING AND VISUALIZATION

(71) Applicants: Tiecheng Zhao, Concord, MA (US); Keiji Ito, Burlingame, CA (US); Ryan Moffitt, Baltimore, MD (US)

(72) Inventors: Tiecheng Zhao, Concord, MA (US); Keiji Ito, Burlingame, CA (US); Ryan Moffitt, Baltimore, MD (US)

(73) Assignee: TeraRecon, Inc., Foster City, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 15/799,470

(22) Filed: Oct. 31, 2017

(65) Prior Publication Data

US 2018/0064505 A1    Mar. 8, 2018

Related U.S. Application Data

(62) Division of application No. 15/007,030, filed on Jan. 26, 2016, now Pat. No. 9,839,490.

(Continued)

(51) Int. Cl.
*A61B 90/00* (2016.01)
*A61B 6/00* (2006.01)
(Continued)

(52) U.S. Cl.
CPC ............ *A61B 90/37* (2016.02); *A61B 6/00* (2013.01); *G06F 19/321* (2013.01); *G06F 19/3481* (2013.01); *G16H 40/63* (2018.01); *A61B 2017/00207* (2013.01); *A61B 2560/0487* (2013.01)

(58) Field of Classification Search
CPC .. A61B 2017/00207; A61B 2560/0487; A61B 6/00; A61B 90/37; G06F 19/321; G06F 19/3481; G16H 40/63; H04B 10/25759; H04B 10/54; H04W 88/085

See application file for complete search history.

(56) References Cited

U.S. PATENT DOCUMENTS

2013/0208955 A1* 8/2013 Zhao ............... G06F 19/321
                                                 382/128
2014/0323845 A1* 10/2014 Forsberg .......... A61B 5/4561
                                                 600/407

OTHER PUBLICATIONS

De Paolis, Lucio T, et al, "Advanced Visualization and Interaction Systems for Surgical Pre-operative Planning," Journal of Computing and Information Technology, Dec. 2010, pp. 385-392.

(Continued)

*Primary Examiner* — Manuchehr Rahmjoo

(57) ABSTRACT

A server receives a request from a client device initiated from a user operating the client device. The server determines a user action identifier (ID) based on the request, the user action ID identifying a user physical action that was captured by one or more sensors. One or more image processing commands are determined based on the user action ID in view of a first medical image currently displayed at the client device. An image processing operation is performed based on the first medical image by executing the one or more image processing commands, generating a second medical image. The second medical image is transmitted to the client device to be presented to the user at the client device.

17 Claims, 20 Drawing Sheets

Related U.S. Application Data

(60) Provisional application No. 62/128,622, filed on Mar. 5, 2015, provisional application No. 62/108,658, filed on Jan. 28, 2015.

(51) Int. Cl.
  G06F 19/00 (2018.01)
  G16H 40/63 (2018.01)
  A61B 17/00 (2006.01)

(56) References Cited

OTHER PUBLICATIONS

Donner, René, et al, "Global Localization of 3D Anatomical Structures by Pre-filtered Hough Forests and Discrete Optimization," Medical Image Analysis, Dec. 2013, pp. 1304-1314.

Ebner, Thomas, et al, "Towards Automatic Bone Age Estimation from MRI: Localization of 3D Anatomical Landmarks", Computer Graphics & Vision, Jul. 9, 2014, pp. 1-10.

Hinckley, Ken, et al, "New Applications for the Touchscreen in 2D and 3D Medical Imaging Workstations," Proc. SPIE Medical Imaging, vol. 2431, Jan. 1995, pp. 110-118.

Neu, Scott C, et al, "Automatic Localization of Anatomical Point Landmarks for Brain Image Processing Algorithms," Neuroinformatics, May 2008, pp. 135-148.

O'Hara, Kenton, et al, "Touchless Interaction in Surgery," Communications of the ACM, vol. 57, No. 1, Jan. 2014, pp. 70-77.

Philips Technology News, "HIH: Hands-free Interaction in the Hospital," <www.medical.philips.com/medicamundi>, Sep. 2005, pp. 58-66.

Rohr, Karl, et al, "Characterization and Localization of Anatomical Landmarks in Medical Images," Proc. 1st Aachen Conf. on Neuropsychology in Neurosurgery, Psychiatry, and Neurology, Dec. 12-14, 1997, 3 pages.

Segundo, Maurício P, et al, "Automatic 3D Facial Segmentation and Landmark Detection," Image Analysis and Processing, Sep. 2007, pp. 431-436.

Subburaj, K, et al, "Automated Identification of Anatomical Landmarks on 3D bone models Reconstructed from CT Scan Images," Computerized Medical Imaging and Graphics, Mar. 2, 2009, pp. 359-368.

Svanfeldt, Gunilla, "A Speech Interface Demonstrator for Pre-operative Planning within Orthopaedic Surgery," Examensarbete i Talkommnukation, Feb. 2002, 35 pages.

Zheng, Yefeng, et al, "Automatic Aorta Segmentation and Valve Landmark Detection in C-Arm CT: Application to Aortic Valve Implantation," Med Image Comput Comput Assist Interv, 2010, pp. 476-483.

\* cited by examiner

| Image ID (optional) ~401 | Action ID ~402 | Medical Image Processing Command(s)/Operation(s) ~403 |
|---|---|---|
| Image #1 | Swipe right-left | Next Image |
| Image #2 | Swipe left-right | Previous Image |
| Image #3 | Swipe diagonal outwardly | Zoom In |
| Image #4 | Swipe diagonal inwardly | Zoom out |
| ... | ... | ... |

| Landmark ID (optional) | Action ID | Medical Image Processing Command(s)/Operation(s) |
|---|---|---|
| Kidney | Action #1 | Retrieve/Render Kidney Image |
| Kidney | Action #2 | Calculate Kidney Volume |
| ... 411 | ... 412 | ... 413 |

| Workflow Stage ID (optional) | Action ID | Medical Image Processing Command(s)/Operation(s) |
|---|---|---|
| Stage #1 | Swipe right-left | Perform operations of next stage (e.g., Stage #2) |
| Stage #4 | Swipe left-right | Perform operations of previous stage (e.g., Stage #3) |
| ... 421 | ... 422 | ... 423 |

FIG. 4C

| User Body Part ID | Action ID | Image/Landmark ID (optional) | Medical Image Processing Command(s)/Operation(s) |
|---|---|---|---|
| Index finger | | Kidney | Retrieve/render kidney image |
| Thumb | | Kidney | Calculate kidney volume |
| Eye | Right-left | | Next image |
| Eye | Left-right | | Previous image |
| ... 431 | ... 432 | ... 433 | ... 434 |

TOUCHLESS ADVANCED IMAGE PROCESSING AND VISUALIZATION

RELATED APPLICATIONS

This application is a divisional of U.S. application Ser. No. 15/007,030, filed Jan. 26, 2016, which claims the benefit of U.S. provisional patent application No. 62/108,658, filed Jan. 28, 2015 and U.S. provisional patent application No. 62/128,622, filed Mar. 5, 2015. The disclosure of the above applications is incorporated by reference herein in its entirety.

FIELD OF THE INVENTION

Embodiments of the present invention relate generally to image processing. More particularly, embodiments of the invention relate to touchless image processing and visualization.

BACKGROUND

Advanced medical imaging processing software allows a user to transform scan images, such as computed tomography (CT), magnetic resonant imaging (MRI), Ultrasound, X-ray, etc. images, into three-dimensional (3D) images as well as other views which help the user interpret the scans. Organs and/or body parts can be isolated, removed, measured, analyzed, viewed, sliced, as well as viewed from any angle, including the interior. For example, cardiac arteries can be measured, analyzed, stenosis identified and measured, and viewed from virtually any perspective. The colon can be analyzed for polyps and "flown" through to evaluate its health. Tumors can be identified and measured, and monitored over time.

However, advanced medical imaging processing software is difficult and labor intensive to use. Generally, the user must be trained to use the specific software, and to perform the specific processing functions. The processing functions often require the use of software tools, a pointing device, such as a mouse, and multiple clicks of the mouse to get the desired results. For example, identifying and measuring a stenosis in a cardiac artery may involve several "click intensive" steps, including bone removal, fragment cleanup, vessel identification, vessel segmentation, stenosis identification, stenosis measurements etc.

A physician may want to perform advanced medical imaging processing in a sterile environment, such as the operating room. For example, a brain surgeon may want to identify the location, size, and other parameters of a brain tumor, and have it on a screen during surgery. He/she may also want to identify the location and size/types of nearby and/or related vasculature. He/she may also want to identify the best entry points of the skull.

In another example, a cardiologist may want to review the cardiovascular vascular before and/or during an angioplasty. He/she may want to see the curvature of the cardiovascular vascular, as well as the aortic access path. He/she may want to see the smoothness/roughness of the stenosis, and/or the degree of stenosis to help choose a catheter/guidewire/stent etc. If the procedure is not going as planned, different views and/or analyses of the anatomy may help in determining options.

However, with current advanced medical imaging processing software, the physician cannot easily, while maintaining sterility, use this type of software. It is currently cumbersome, time consuming, and risky, sterility-wise, for a physician to use such software in a sterile environment, especially with a patient on the table. There is a need for a physician and/or technician in a sterile environment, to easily, quickly, safely and accurately, obtain results from advanced medical image processing software, while maintaining the sterile environment.

BRIEF DESCRIPTION OF THE DRAWINGS

Embodiments of the invention are illustrated by way of example and not limitation in the figures of the accompanying drawings in which like references indicate similar elements.

FIGS. 4A-4D are diagrams illustrating various action to command/operation mapping data structures according to certain embodiments of the invention.

DETAILED DESCRIPTION

Figure 1:
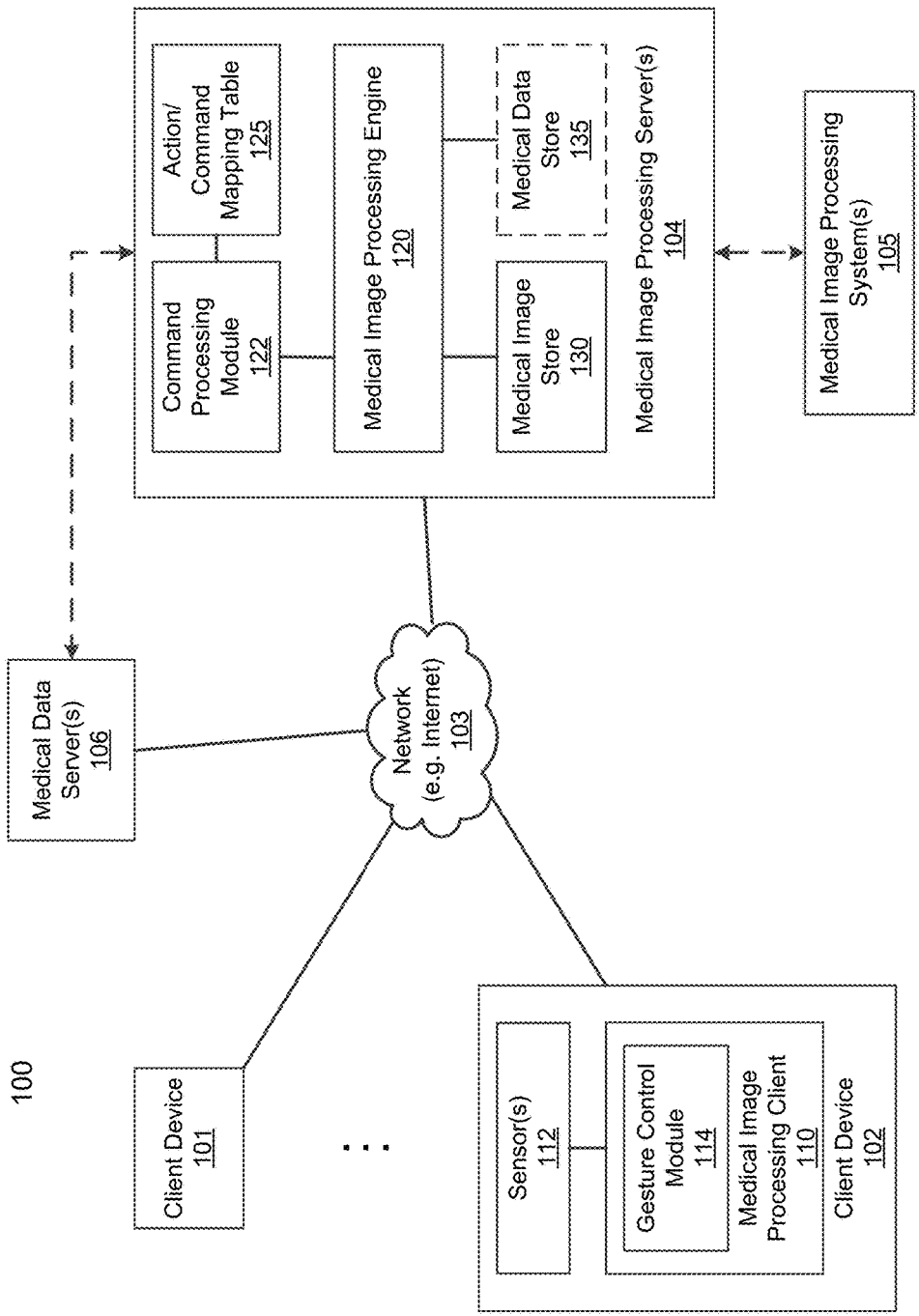
FIG. 1 is a block diagram illustrating an example of a touchless advanced image processing (TAIP) system according to one embodiment of the invention.

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

According to some embodiments, a touchless advanced image processing (TAIP) system is utilized to allow a user in a sterile, or otherwise limiting environment, to control advanced imaging processing operations using "touchless" controls. Touchless controls may include voice, motion (e.g., hand or eye gestures) or other types of controls such as accelerometer-based or gyroscope-based sensors or devices. According to one embodiment, the TAIP system takes advantage of automatic image processing functionalities based on identified parameters and automatically identified anatomical landmarks.

According to one embodiment, a TAIP system is implemented as an image processing server that provides image processing services to a variety of client devices over a network, where the image processing server can be implemented as a part of a cluster of cloud servers. Each client device may deploy an image processing client application or software. One or more sensors may be deployed within or communicatively coupled to each of the client devices to detect a user motion or user action of a user operating the client device, without requiring the user to physically touch or contact the client device (e.g., mouse, keyboard, display device). A sensor can be any one or more of an audio sensor (e.g., microphone), a visual sensor (e.g., camera), an infrared sensor, or a motion detector, etc.

In response to a signal received from one or more sensors, a gesture control module of a client device determines a user action or motion (e.g., a physical action or motion of a user operating the client device) represented by the signal (e.g., swipe left or swipe right). A command processing module of the client device determines whether the user action is valid in view of a first medical image currently displayed at the client device. The determination may be performed based on a list of previously configured user actions. The user actions may be associated with or assigned to the first medical image or one or more landmarks associated with the first medical image. If it is determined that the user action is valid, the client device transmits a request for image processing to an image processing server over a network. The request may include a user action identifier (ID) identifying the user action of the user operating the client device and optional an ID identifying the first medical image or an ID identifying one or more landmarks of the first medical image.

In response to the request, according to one embodiment, a command processing module of the image processing server interprets the user action in view of metadata or a landmark of the first medical image to determine one or more image processing operations or image process commands. In one embodiment, an action to command (action/command) mapping table or an action to operation (action/operation) mapping table or data structure, which has been previously configured, may be utilized to map a particular user action to one or more image processing commands or image processing operations. An image processing engine of the image processing server then performs the determined image processing operations based on the first medical image including, for example, a measurement based on one or more landmarks associated with the first medical image. A second medical image is generated as a result and the second medical image is then transmitted from the image processing server to the client device. The client device then displays the second medical image, as well as other medical information associated with the second medical image and/or the corresponding patient. All of the above operations are performed and communicated between the client device and the image processing server without requiring the user of the client device to physically contact the client device.

FIG. 1 is a block diagram illustrating an example of a touchless advanced image processing (TAIP) system according to one embodiment of the invention. Referring to FIG. 1, system 100 includes, amongst others, a variety of client devices 101-102 communicatively coupled to image processing server 104 over network 103, wired or wirelessly. Network 103 may be a local area network (LAN), a metropolitan area network (MAN), a wide area network (WAN) such as the Internet or an intranet, a private cloud network, a public cloud network, or a combination thereof. Although there are two client devices 101-102 shown in FIG. 1, more or fewer client devices may be coupled to image processing server 104. Similarly, although only one image processing server 104 is shown, more image processing servers may also be utilized to provide medical image processing services to clients 101-102. For example, image processing server 104 may be implemented as one of a cluster of servers (e.g., cloud servers) to provide image processing services in a distributed fashion (e.g., software as service or SaS).

Client devices 101-102 may be deployed at users' locations, such as doctors or physicians' offices or operating rooms of hospitals. Each of client devices 101-102 includes a medical image processing client 110 hosted therein. For the purpose of illustration, details of client device 102 will be described herein. However, the description can be equally applicable to client device 101. Image processing client 110 provides a graphical user interface (GUI) to present medical images to users of client device 102, where the medical images are generated and processed by image processing server 104 in response to user requests in a client-server fashion. For example, a user (e.g., a doctor) can log into his/her account in image processing server 104 from client device 102 via client image processing client 110. From image processing client 110, the user can request certain images of a patient to be retrieved from or processed at image processing server 104. Image processing client 110 then transmits proper commands or requests to image processing server 104. In response, image processing server 104 performs related image processing operations and transmits the requested images as a result back to client 102.

In one embodiment, client device 102 includes or is coupled to one or more sensors 112. Sensors 112 may be deployed or mounted at various locations within an operating environment of a user (e.g., a doctor's office, an operating room of a hospital), which are configured to capture user actions or physical movements of the user. The captured user actions represent certain user interactions with image processing client 110, without requiring the user to physically contact or touch client device 102. Sensors 112 can be any kind of sensors that can capture user actions without physical touching. Sensors 112 may be any one or more of an audio sensor (e.g., microphone), a visual sensor (e.g., a camera), an infrared sensor, a motion detector, or a combination thereof. Any of sensors 112 may be coupled to client device 102 via an input and output (IO) interface, a bus, or a network interface, wired or wirelessly.

According to one embodiment, image processing client 110 further includes or is coupled to a gesture control module 114, which may be implemented as a standalone module or may be integrated within image processing client 110. Gesture control module 114 is adapted to receive a signal from one or more sensors 112, to interpret the signals, to determine a user action based on the signal, and/or to communicate the user action to image processing client 110. The signal is received from one or more of sensors 112, which capture the user actions or physical movements of the user without the user physically touching client device 102.

In response to the user action determined by gesture control module 114, image processing client 110 determines whether the user action is valid in view of the medical image currently displayed. Note that not all user actions can be recognized as valid actions. In one embodiment, there may be a list of predetermined actions that can be utilized as valid user actions for interacting image processing client 110. The list of predetermined actions may be preconfigured by a user (e.g., user preference), an administrator (e.g., a system or product provider), or a product developer of image processing client 110. If the user action is not found in the list of preconfigured user actions, the user action may be considered as invalid. If a user action is deemed to be invalid, an alert or indication (e.g., message, audio sound) may be presented to the user.

If it is determined that the user action is valid, according to one embodiment, image processing client 110 transmits a user action ID representing the recognized user action to image processing server 104 requesting image processing server 104 to perform an image processing operation that is associated with the user action. Image processing client 110 may further transmit to image processing server 104 an image ID identifying an image currently displayed at client device 102, a landmark of the displayed image, or any other metadata of the displayed image to allow image processing server 104 to ascertain or identify the image that is currently displayed at client device 102.

Image processing client 110 may further transmit certain patient or medical information of a patient associated with the displayed image (e.g., a patient ID, a body part ID, a medical procedure ID) to image processing server 104. The patient or medical information may be obtained from a variety of medical data servers or data sources 106. For example, medical data server(s) 106 may represent any one or more of a laboratory information system (LIS), a radiology information system (RIS), an enterprise content management (ECM) system, an electronic medical record (EMR) system, a hospital information system (HIS), a picture archiving and communication system (PACS), or a vendor neutral archive (VNA) system. Alternatively, image processing client 110 may transmit a patient ID identifying a patient associated with the image currently displayed. Image processing server 104 can then communicate with medical data servers 106 to obtain the related medical information and optionally store in medical data store 135. In one embodiment, image processing client 110 may be integrated with a medical information client (e.g., medical record client) that can access both the medical data systems and image processing server 104.

In response to the request, command processing module 122 examines the request to determine the user action. Based on the user action and metadata of the medical image currently displayed at client device 102, command processing module 122 determines one or more image processing commands or operations that are associated with the user action and the metadata of the displayed medical image (e.g., a landmark, an image ID). In one embodiment, command processing module 122 performs a lookup operation in action/command mapping table or data structure 125 based on the user action and the metadata of the image to determine a list of one or more image processing commands or image processing operations. Such mapping table 125 may be preconfigured on a variety of basis, such as, per image basis, per landmark basis, per user basis, per patient basis, per workflow basis, or a combination thereof.

Command processing module 122 then communicates the information of the image processing instructions, commands, or operations to medical image processing engine 120. Image processing engine 120 then performs the requested image processing operations. The image processing operations can be a variety of image processing operations. In one embodiment, an image processing operation can be retrieving another image or related image based on the image currently presented at client device 102. An image processing operation can be performing a measurement of a body part associated with the image currently presented (e.g., also referred to as a first image). As a result of an image processing operation, image processing engine 120 may generate a new image, where the images generated by image processing engine 120 may be maintained in image store 130. Image processing engine 120 may perform additional operations based on medical information of a patient associated with the currently displayed image. The medical information may be obtained from medical data sources 106 and optionally maintained as part of medical data store 135. The new image (also referred to as a second image) is then transmitted from image processing server 104 to client device 102 to be presented to the user.

Note that image processing engine 120 may include a variety of image processing tools for processing medical images, which will be described in details further below. Image processing engine 120 may offload at least some of the image processing operations to one or more backend or dedicated image processing systems 105. Backend or dedicated image processing systems 105 may have higher processing power and resources. As a result, a user does not have to touch client device 102 in order to interact with image processing client 110 and to obtain image processing services from image processing server 104.

Also note that the configuration as shown in FIG. 1 is described for the purpose of illustration only. Other configurations may also exist. For example, according to another embodiment, instead of performing at a client device, the determination of whether a particular user action is valid may be performed at the image processing server 104 in a centralized manner. In such an embodiment, a client may just forward a user action ID identifying a user action to server 104. Server 104 then determines whether such a user action is valid in view of the image currently displayed at the client. Server 104 then informs the client the result of the determination. In a further embodiment, action/command mapping table 125 may be downloaded and maintained by the client. In such embodiment, it is the client's responsible to interpret the user action and convert the user action into one or more image processing commands. The client then transmits the image processing commands to server 104 to execute the commands.

Figure 2:
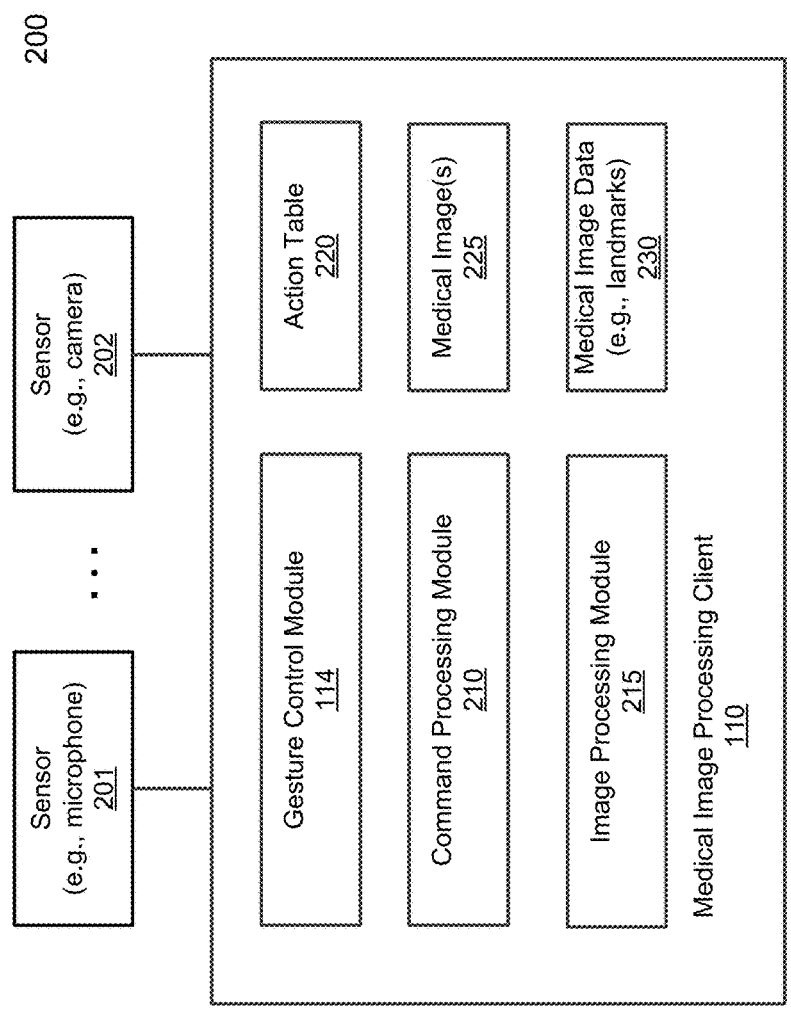
FIG. 2 is a block diagram illustrating an example of a client device according to one embodiment of the invention.

FIG. 2 is a block diagram illustrating an example of a client device according to one embodiment of the invention. Client device 200 may represent any of client devices 101-102 of FIG. 1. Referring to FIG. 2, according to one embodiment, client device 200 includes, but is not limited to, image processing client 110 coupled to one or more sensors 201-202. Image processing client 110 may be implemented in software, hardware, or a combination of both. For example, image processing client 110 may be a client application, which may be loaded into a system memory and executed by one or more processors of client device 200 (not shown).

In one embodiment, sensors 201-202 can be any kind of sensors that can capture user actions without physical touching. Sensors 201-202 may be any of an audio sensor (e.g., microphone), a visual sensor (e.g., a camera), an infrared sensor, a motion detector, or a combination thereof. These sensors 201-202 may be mounted on various locations of an operating environment in which client device 200 is operating, such as, for example, doctors or physicians' offices or operating rooms of hospitals. Alternatively, at least some of sensors 201-202 may be mounted or attached to a body of a user, such as, glasses, helmet worn by the user (e.g., eye movement tracking, facial or emotion recognition). Any of sensors 201-202 may be communicatively coupled to client device 200 via an input and output (IO) interface or controller, a bus, or a network interface. Examples of such interfaces include a keyboard controller, a mouse controller, a universal serial bus (USB) port, a chipset, etc. Sensors 201-202 may be physically or wirelessly connected to client device 200. Sensors 201-202 may be configured to capture user actions or physical movements of the user. The captured user actions represent certain user interactions with image processing client 110, without requiring the user to physically contact or touch client device 200.

According to one embodiment, image processing client 110 further includes or is coupled to a gesture control module 114, which may be implemented as a standalone module or integrated within image processing client 110. Gesture control module 114 is adapted to monitor and/or receive one or more signals from one or more of sensors 201-202, to interpret the signals, to determine one or more user actions based on the signals, and to communicate the user actions to image processing client 110. The signals may be received from one or more of sensors 201-202, which capture the user actions or physical movements of the user (e.g., finger, arm, and/or eye movements) without the user physically touching client device 200. Gesture control module 114 may be configured or programmed with a necessary algorithm or model, which may be stored as executable instructions in a machine-readable medium to interpret the user gestures or user interactions, particularly for image processing purposes.

Gesture recognition is a topic in computer science and language technology with the goal of interpreting human gestures via mathematical algorithms. Gestures can originate from any bodily motion or state but commonly originate from the face or hand. Gesture recognition enables humans to communicate with the machine and interact naturally without any mechanical devices. Using the concept of gesture recognition, it is possible to point finger at the computer screen so that the cursor will move accordingly. With gesture recognition, a user can also interact with a keyboard or keyboard controller via a virtual keyboard displayed on the screen.

Referring back to FIG. 2, gesture control module 114 can determine multiple user gestures or user actions (e.g., audio, visual recognition, motion detection). Such multiple user actions may be individually or collectively interpreted and utilized to determine a user intent of the user in terms of what image processing operations the user wishes the image processing server to perform, etc.

In response to the user action determined by gesture control module 114, command processing module 210 determines whether the user action is valid in view of medical image(s) 225 currently displayed by image processing module 215. Image processing module 215 is responsible for receiving images from an image processing server, rendering and presenting the images to a display device of client device 200 (not shown). Note that not all user actions can be recognized as valid actions. In one embodiment, image processing client 110 maintains action table or action data structure 220, which stores a list of predetermined actions that can be utilized as user actions for interacting image processing client 110.

The list of actions may be configured the same for all image processing. Alternatively, the list of actions may be different from one image to another image, from one landmark to another landmark, and/or from one user to another user. For example, for a given image or a given type of images, there may be a different list of actions available or defined for manipulating and requesting image processing operations. Similarly, for a different user, different user preferences or user settings may be applied to define what user actions are related to which of the image processing operations intended by that particular user. A user may be able to individually define a particular action to initiate a particular image processing operation. Furthermore, for a multi-tenant operating environment (e.g., cloud-based services such as software as service or SaS), each tenant (e.g., enterprise tenant) may define a specific list of actions for the members of that particular tenant. There may be a set of base settings that are shared by multiple users and/or images/landmarks. In addition, a particular user and/or image/landmark may have a set of individual settings that may override or compliment the base settings.

The list of predetermined actions in action table 220 may be preconfigured by a user (e.g., with user preference), an administrator (e.g., a system or product provider), or a product developer of image processing client 110. Action table 220 may be configured at the image processing server and downloaded to client device 200, or vice versa. Action table 220 may be stored in a persistent storage device of client device 200 such as a hard disk and loaded into a system memory for accessing (not shown). Note that the list of actions can be maintained in a variety of data structures such as databases, etc.

If the user action is not found in the list of preconfigured user actions, the user action may be considered as invalid. If a user action is deemed to be invalid, an alert or indication (e.g., message, audio sound) may be presented to the user. The user can then perform another gesture or action to interact with image processing client 110. In one embodiment, image processing client 110 may display a list of valid actions available to the display image and/or the current user for selection, for example, in response to a user request for the list.

If it is determined that the user action is valid, according to one embodiment, command processing module 210 or image processing module 215 transmits one or more user action IDs representing one or more recognized user actions to an image processing server (e.g., image processing server 104) requesting the image processing server to perform one or more image processing operations that are associated with the user actions. Image processing client 110 may further transmit to the image processing server certain metadata describing an image currently displayed at client device 200, a landmark of the displayed image, or any other metadata of the displayed image (collectively referred to as medical image data 230) to allow the image processing server to ascertain or identify the image that is currently displayed at client device 200, in order to determine appropriate image processing commands or operations.

Image processing client 110 may further transmit certain patient or medical information of a patient associated with the displayed image (e.g., a patient ID, a body part ID, a medical procedure ID) to the image processing server. The patient or medical information may be obtained from a variety of medical data servers or data sources (e.g., medical data sources 106 of FIG. 1). A new image and/or new medical data may then be received from the image processing server as a result of image processing operations. The new image and/or the medical data are presented by image processing module 215 at the display device of client device 200, and the above processes may be repeatedly performed.

Figure 3:
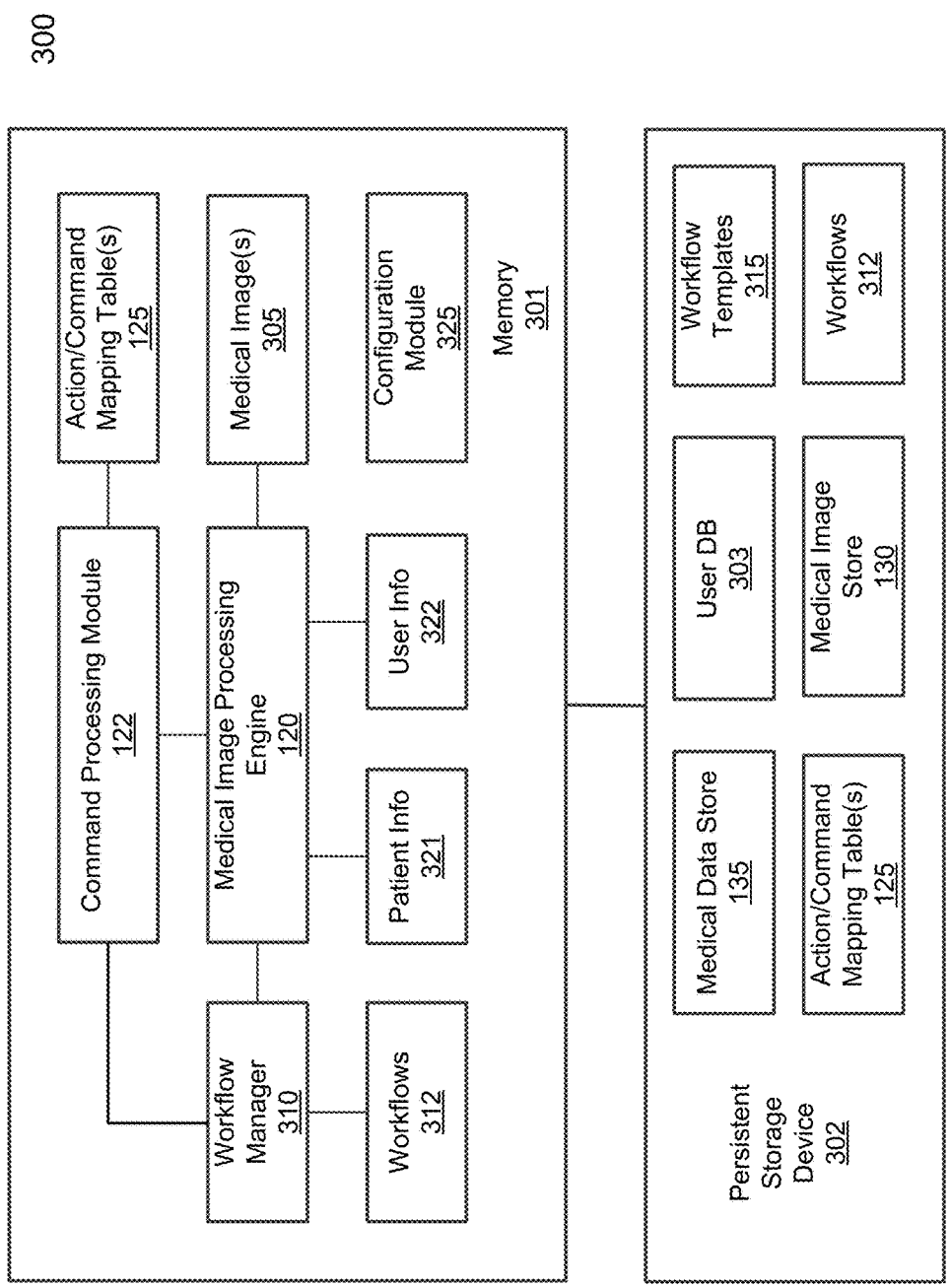
FIG. 3 is a block diagram illustrating an example of an image processing server according to one embodiment of the invention.

FIG. 3 is a block diagram illustrating an example of an image processing server according to one embodiment of the invention. System 300 may represent image processing server 104 of FIG. 1. Referring to FIG. 3, in this example, system 300 includes command processing module 122 and image processing engine 120 loaded in memory 301 and executed by one or more processors (not shown). Note that image processing engine 120 may be implemented in dedicated hardware having dedicated processing power and resources (e.g., processors and memory) for image processing. Image processing server 300 further maintains an action/command or action/operation mapping table 125, which may be implemented in a variety of data structures. Mapping table 125 maps a particular user action to one or more image processing commands or operations. Such mapping may further be based on a particular image or image data (e.g., image ID, landmark, or other image metadata) currently presented at a client device.

As described above, when a user performs a particular user action in front of one or more sensors without touching a client device, the user action is captured by the sensors and processed by a gesture control module and command processing module of the client device. If it is determined such a user action is valid, the client device sends a request for image processing to an image processing server such as image processing server 300. The request may include one or more user action IDs identifying one or more captured user actions and optional image metadata (e.g., an image ID, landmark(s)) describing an image currently displayed at the client device.

In response to the request, command processing module 122 examines the request to determine one or more user actions performed by the user at the client device. Based on the user action and metadata of the medical image currently displayed at the client device, command processing module 122 determines one or more image processing commands or operations that are associated with the user action and the metadata of the displayed medical image (e.g., a landmark, an image ID). In one embodiment, command processing module 122 performs a lookup operation in action/command mapping table or data structure 125 based on the user action and the metadata of the image to determine a list of one or more image processing commands or image processing operations. Such mapping table 125 may be preconfigured based on a variety of factors. For example, mapping table 125 may be configured per image basis, per landmark basis, per user basis, per patient basis, per workflow basis, or a combination thereof. Examples of mapping table 125 are shown in FIGS. 4A-4D. Mapping table 125 may be configured by a user, an administrator of a tenant, or a system administrator associated with server 300 using configuration module 325, for example, via a variety of configuration interfaces (e.g., Web, application programming interface or API, command line interface or CLI). The configured mapping tables may be stored in persistent storage device 302.

According to one embodiment, since image processing server 300 provides images to a variety of client devices to be displayed therein, image processing server 300 may maintain or know which of the images 305 that is currently displayed at a particular one of the client devices. As a result, a client device may only need to transmit a request having the user action or actions therein without having to specify which image is currently displayed. Command processing module 122 may determine the image currently displayed at the client device, for example, by communicating with image processing engine 120 via an API. However, if certain image processing commands or operations are based on a particular landmark and the currently displayed image contains multiple landmarks, the client device may have to specify which of the landmarks is associated with the user action or actions. Alternatively, command processing module 122 and/or image processing engine 120 may automatically determine the corresponding landmark(s), for example, based on user settings, user preferences, or prior user interactions. Furthermore, if the currently displayed image is associated with a particular workflow stage of an image processing workflow, the client device may specify a workflow stage ID identifying that particular workflow stage.

Based on the image processing commands or operations determined based on mapping table 125, command processing module 122 communicates the information of the image processing instructions, commands, or operations to medical image processing engine 120. Image processing engine 120 then performs the requested image processing operations. The image processing operations can be a variety of image processing operations. In one embodiment, an image processing operation can be retrieving another image or related image based on the imager currently presented at client device 102. An image processing operation can be performing a measurement of a body part associated with the image currently presented (e.g., also referred to as a first image). For example, an image processing operation can be measuring a volume of a kidney.

According to one embodiment, an image that is currently displayed at a client device may be associated with a particular workflow stage of an image processing workflow. The request received from the client device may further include a workflow stage ID identifying a particular workflow stage of a particular workflow. In response to the request, command processing module 122 and/or image processing engine 120 may communicate with workflow manager 310 to determine what image processing operations associated with that particular workflow stage or what the next workflow stage is, dependent upon the instructions received from the client device. The workflow stages may be defined in a corresponding one of workflows 312. Workflow manager 310 then determines one or more image processor operations associated with the identified workflow stage based on the corresponding workflow. Image processing engine 120 then performs the image processing operations accordingly. Note that workflow manager 310 may be integrated within image processing engine 120.

In one embodiment, workflow manager 310 manages the creation, update and deletion of workflow templates. It also performs workflow scene creation when receiving user requests to apply a workflow template to medical image data. A workflow is defined to capture the repetitive pattern of activities in the process of generating medical image views for diagnosis. A workflow arranges these activities into a process flow according to the order of performing each activity. Each of the activities in the workflow has a clear definition of its functions, the resource required in performing the activity, and the inputs received and outputs generated by the activity. Each activity in a workflow is referred to as a workflow stage, or a workflow element. With requirements and responsibilities clearly defined, a workflow stage of a workflow is designed to perform one specific task in the process of accomplishing the goal defined in the workflow. For many medical image studies, the patterns of activities to produce medical image views for diagnosis are usually repetitive and clearly defined. Therefore, it is advantageous to utilize workflows to model and document real life medical image processing practices, ensuring the image processing being properly performed under the defined procedural rules of the workflow. The results of the workflow stages can be saved for later review or use.

In one embodiment, a workflow for a specific medical image study is modeled by a workflow template (e.g., workflow templates 315). A workflow template is a template with a predefined set of workflow stages forming a logical workflow. The order of processing an activity is modeled by the order established among the predefined set of workflow stages. In one embodiment, workflow stages in a workflow template are ordered sequentially, with lower order stages being performed before the higher order stages. In another embodiment, dependency relationships are maintained among the workflow stages. Under such arrangement, a workflow stage cannot be performed before the workflow stages it is depending on being performed first. In a further embodiment, the advanced workflow management allows one workflow stage depending on multiple workflow stages, or multiple workflow stages depending on one workflow stage, etc.

The image processing operations receive medical image data collected by the medical imaging devices as inputs, process the medical image data, and generate metadata as outputs. Metadata, also known as metadata elements, broadly refers to parameters and/or instructions for describing, processing, and/or managing the medical image data. For instance, metadata generated by the image processing operations of a workflow stage includes image processing parameters that can be applied to medical image data to generate medical image views for diagnostic purpose. Further, various automatic and manual manipulations of the medical image views can also be captured as metadata. Thus, metadata allows the returning of the system to the state it was in when the metadata was saved. After a user validates the results generated from processing a workflow stage predefined in the workflow template, workflow manager 310 creates a new scene and stores the new scene to the workflow scene. The workflow manager 310 also allows the updating and saving of scenes during user adjustments of the medical image views generated from the scenes.

Referring back to FIG. 3, as a result of an image processing operation, image processing engine 120 may generate a new image, where the images generated by image processing engine 120 may be maintained in image store 130 stored in persistent storage device 302. Image processing engine 120 may perform additional operations based on medical information 321 of a patient associated with the currently displayed image. The medical information may be obtained from a variety of medical data sources and optionally maintained as part of medical data store 135. The new image (also referred to as a second image) is then transmitted from image processing server 300 to the client device to be presented to the user. Additional operations may be performed further based on user information 322 of a user that operates the client device, such as, for example, user preferences of the user. User information 322 may be maintained as part of user database 303. User database 303 stores a variety of user information of a variety of users who are authenticated and authorized to use the resources (e.g., image processing tools) provided by image processing server 300. Prior to using the image processing resources of image processing server 300, a user has to log in to its account to be authenticated and authorized by an access control module (not shown).

As described above, with gesture control, a variety of user actions or motions can be configured to be associated with various image processing commands or processing operations. Gesture control can allow a user to operate a computer and/or software on the computer (e.g., a workstation, tablet, mobile device, laptop, or any combination thereof) without physically touching the computer. Gesture control can control the computer by the user's motion of the body and/or body parts (e.g., hands, fingers, arms, feet, eye, or any combination thereof). Gesture control can operate the computer by using cameras on the computer or cameras physically separated from the computer to detect the user's motion. The user's motion detected by the camera can be interpreted by the system software and/or server to complete a specific command. There can be one camera or a plurality of cameras.

For example, if the user swipes his hand from right to left, the camera can detect the swipe motion. The swipe motion can then be examined by the client application (e.g., image processing client) or the server (e.g., image processing server) to ensure the swipe motion is a valid motion to be processed. If the motion is valid, the swipe motion signal can be sent to the server to be processed. The swipe motion can correlate to displaying the next image (e.g., next workflow). The next display and/or image can be sent from the server to the client application. The client application can then display on a screen the new display/image based on the user's right to left swipe.

Gesture control can operate by using audio tools (e.g., a plurality of speakers and/or microphones located within the computer or physically separated from the computer). The speakers can emit ultrasound which will bounce to microphones such that it can track the user's motions (e.g., hand movements) which can be interpreted by the system software to complete a specific command. Gesture control can operate by using infrared technology to track the user's motion.

The system software can also recognize a first body part of the user correlating with displaying a specific area of the preloaded images. The preloaded images can be pre-processed by the back-end server to create landmarks. Landmarks can correlate with specific areas of the preloaded image (e.g., a first landmark can correlate with a liver, a second landmark can correlate with the aorta). For example, the first finger of the user can represent the kidney and/or the second finger of the user can represent the kidney volume. When the user manipulates the first finger in front of the gesture control sensor (e.g., camera, speaker, microphone, infrared sensor, or any combination thereof), the client application, software, and/or server can process this such that the client application displays the kidney on the computer screen. When the user manipulates the second finger in front of the gesture control sensor, the client application, software, and/or server can process and calculate this such that the client application displays the kidney volume.

Eye tracking can be a sensor technology that can enable the computer to know exactly where your eyes are focused/moved. Eye tracking can be a remote or head mounted eye tracker connected (e.g., wirelessly or wired) to the computer. Eye tracking can have a light source (e.g., infrared) and/or a camera, or any other currently available method. The camera and/or sensor can track the reflection of the light source along with visible ocular features such as the pupil. Such information can be used to determine the rotation of the eye and/or direction of the gaze. The sensor, light source and/or camera can analyze the visual path of the eye of the user.

Touchless technology can include a touchless trackpad to control the computer. Touchless trackpad can be wireless. For example, the touchless trackpad can have a camera, audio tools, and/or infrared sensors such that the user can make gestures towards the trackpad and the trackpad can then send such signal to control the client application on the computer and/or the computer. The trackpad can be in close proximity to the user (e.g., in the sterile field). Such commands can be mapped to various user actions or motions via appropriate mapping data structures as described above.

FIGS. 4A-4D are examples of action mapping data structures according to certain embodiments of the invention. The mapping data structures as shown in FIGS. 4A-4D can represent any of the action mapping tables described above (e.g., mapping tables 125). Referring to FIG. 4A, mapping table 400 maps certain actions of certain images to a set of one or more image processing commands or image processing operations. Mapping table 400 includes multiple entries, each entry includes image ID 401, action ID 402, and a set of one or more image processing commands or image processing operations 403. When a request is received from a client device, an action ID of a user action and an optional image ID of an image currently displayed at the client device are determined. Based on the action ID and image ID, a matching entry is located by looking up based on fields 401-402. A set of image processing commands or processing operations 403 is determined. In this example as shown in FIG. 4A, a user action of a wipe from right to left will indicate that a user would like to receive a next image with respect to a current image identified by image ID 401. Similarly, a user action of a swipe from left to right will return a previous image of a current image identified by image ID 401. User actions of a swipe diagonal outwardly and inwardly will be interpreted as a zoom-in and a zoom-out command respectively.

Referring now to FIG. 4B, mapping table 410 maps a particular landmark 411 of a particular image and a particular user action 412 to a set of one or more image processing commands or image processing operations 413. For example, if there is a landmark in an image currently displayed at a client device, a certain user action will cause an image associated with the landmark to be retrieved or processed. In this example, a first user action on a landmark associated with a kidney will be interpreted as a command to retrieve or render a kidney image, while a second user action on the same landmark may be interpreted as a command to calculate a kidney volume.

Mapping table 420 of FIG. 4C maps a particular workflow stage 421 and a particular user action 422 to a set of one or more image processing commands or image processing operations 423. In this example, based on a current workflow stage identified by workflow stage ID 421, a user action of a wipe from right to left will be interpreted as a command to perform one or more operations associated with a next workflow stage. Similarly, a user action of a swipe from left to right will be interpreted as a command to perform one or more operations associated with a previous workflow stage.

Mapping table 430 of FIG. 4D maps a particular user body part 431 and/or a particular user action 432 of the body part on a particular landmark or image 433 to a set of one or more image processing commands or image processing operations 434. For example, if a user points or uses an index finger, such an index finger may be recognized and interpreted as a command to retrieve or render a kidney image. Similarly, if the user uses its thumb or another finger, it may be interpreted as a command to calculate kidney volume. The above described techniques may also be applied to eye movements.

Note that the mapping data structures as shown in FIGS. 4A-4D are described for illustration purposes only. More or fewer mapping data structures, different formats, and/or different mapped actions may be configured and utilized. Some of the above mappings or gesture controls can be utilized individually or in combination, dependent upon the specific configurations.

Figure 5A:
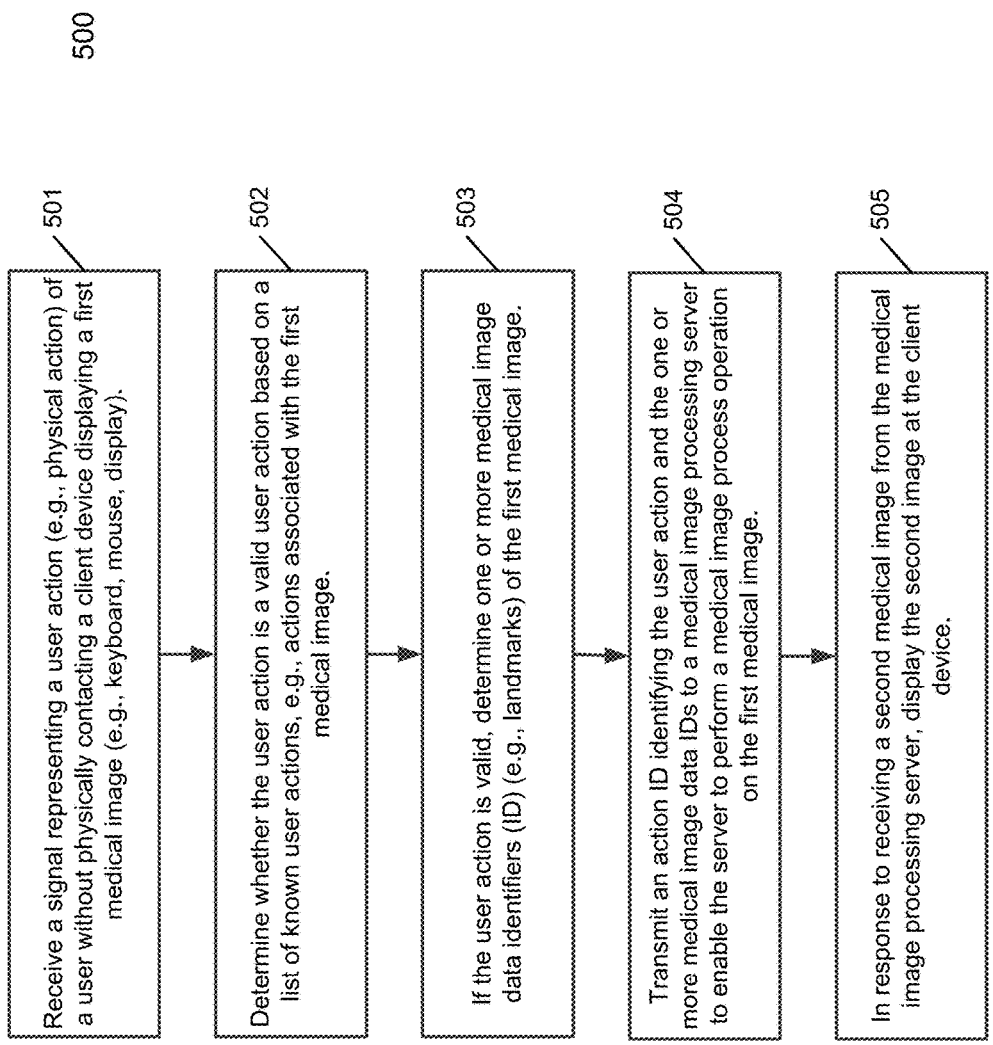
FIGS. 5A-5B are flow diagrams illustrating a process of touchless image processing according to certain embodiments of the invention.

FIG. 5A is a flow diagram illustrating a process of touchless image processing according to one embodiment of the invention. Process 500 may be performed by processing logic that may include software, hardware, or a combination thereof. For example, process 500 may be performed by a client device such as client devices 101-102 described above. Referring to FIG. 5A, at block 501, processing logic receives a signal representing a user action (e.g., physical action) of a user without physically contacting a client device (e.g., mouse, keyboard, display device). The client device currently displays a first medical image that was processed and received from a remote image processing server. At block 502, processing logic determines whether the user action is a valid action based on a list of known actions that have been configured previously. The list of known actions may be associated with the first medical image currently displayed.

If the user action is valid (e.g., found in the list of known actions), at block 503, processing logic determines one or more medical image data IDs of the first medical image. A medical image data ID can be an image ID identifying the first image or a landmark ID identifying a landmark within the first image. At block 504, processing logic transmits an action ID identifying the user action and optional one or more image data IDs to an image processing server to enable the image processing server to determine and perform one or more image processing operations related to the first image. In response to receiving a second image from the image processing server, at block 505, processing logic displays the second image at the client device.

Figure 5B:
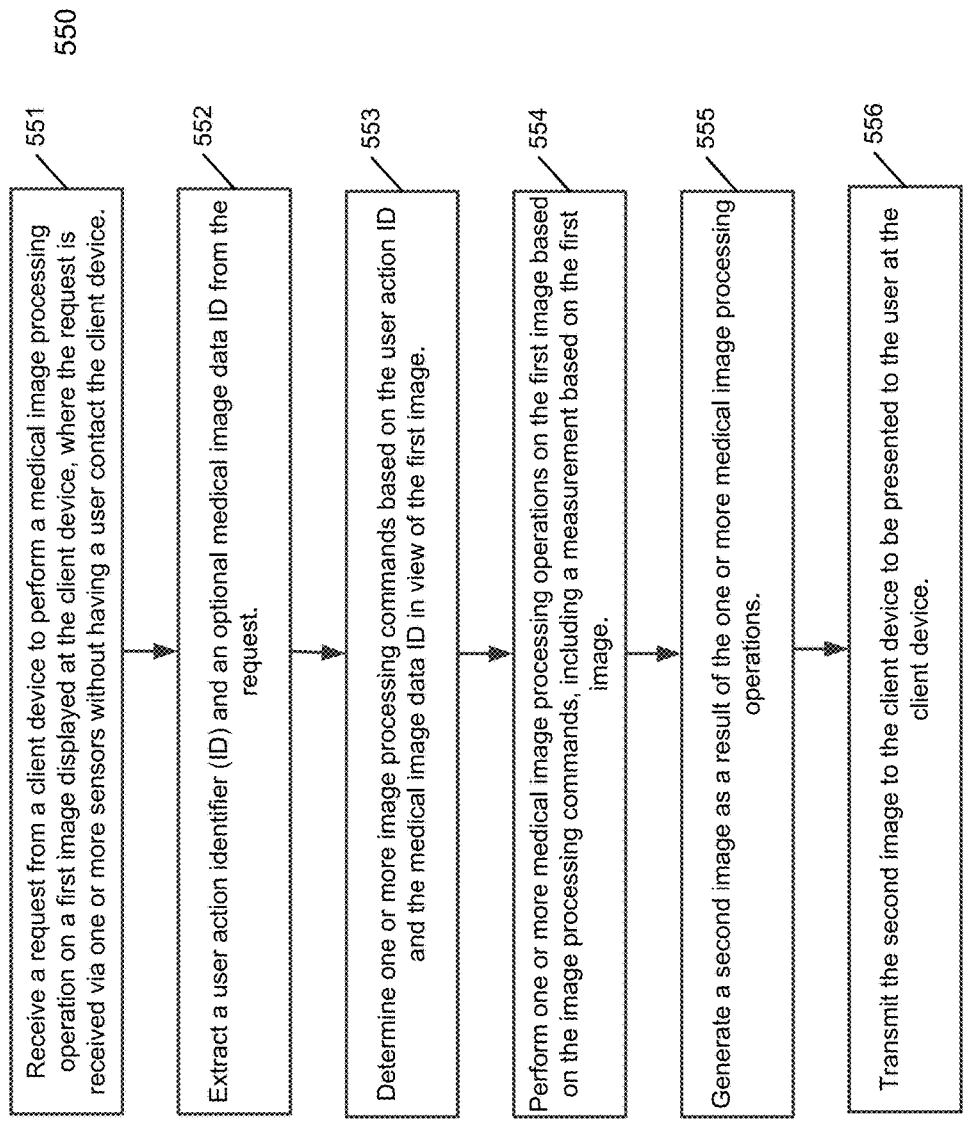

FIG. 5B is a flow diagram illustrating a process of touchless image processing according to one embodiment of the invention. Process 550 may be performed by processing logic that may include software, hardware, or a combination thereof. For example, process 550 may be performed by an image processing server such as server 104 of FIG. 1 described above. Referring to FIG. 5B, at block 551, processing logic receives a request from a client device to perform a medical image processing operation based on a first medical image displayed at the client device. The request is received via one or more sensors that captured a user action of a user operating the client device, without having the user physically contact the client device. At block 552, processing logic extracts an action ID and an optional image data from the request.

At block 553, processing logic determines one or more image processing commands or operations based on the user action ID and/or image data ID in view of the first image. In one embodiment, processing logic may perform a lookup operation in one or more action/command or action/operation mapping tables to determine the image processing commands or operations. At block 554, processing logic performs the one or more image processing operations based on the image processing commands. The image processing operations may include performing a measurement of a body part represented by the first image, which may be identified by the image data ID (e.g., landmark). At block 555, a second image is generated as a result of the image processing operations and at block 556, the second image is transmitted to the client device to be presented thereon.

The techniques described above can be applied to a variety of image processing commands or operations. One of the most popular gesture controls is voice interactive controls. An image processing server can communicate with an image processing client to provide an interactive dialog mechanism with a user in processing the user interactions represented by the gestures. A user can speak to a microphone coupled to the image processing client to instruct the system to perform certain actions. Similarly, the system can query or prompt the user for instructions via a speaker or displayed messages.

For example, if a physician is not satisfied with the system's automatic segmentation of an organ, rather than attempting to change it point by point, he/she can instead issue endpoint-oriented commands such as "smooth results," "expand results," "contract results," "move results," "change landmark," "change view", etc. These words can be recognized by a voice or speech recognition system or a speech-to-text module and interpreted by a command processing module as described above. Other things that can be changed with touchless commands include changing how the images are processed (changing the processing flow), changing the result, and changing the endpoint. In addition, results can be added to results. For example, a physician can ask for a summary of the stenosis in the vessels of a heart, and then he/she can ask for a calcium score. Both can be viewed simultaneously if desired.

According to another embodiment, the system can also take advantage of pre-built workflow elements. For example, in EVAR (Endo-vascular aneurysm repair) procedure, surgeons need to look the front- and back-views of abdominal aorta, left and right renal arteries and iliac arteries. The system can be set up to pre-build these views, and allows easy "next" and "previous" or similar commands or motion to further simplify the navigation in commands, gestures or devices used. The system is able to automatically detect anatomical landmarks, automatically perform advanced image processing, automatically incorporate a user's preferences/parameters, and importantly, make adjustments and additions to the results based on the user's simple commands.

Figure 6:
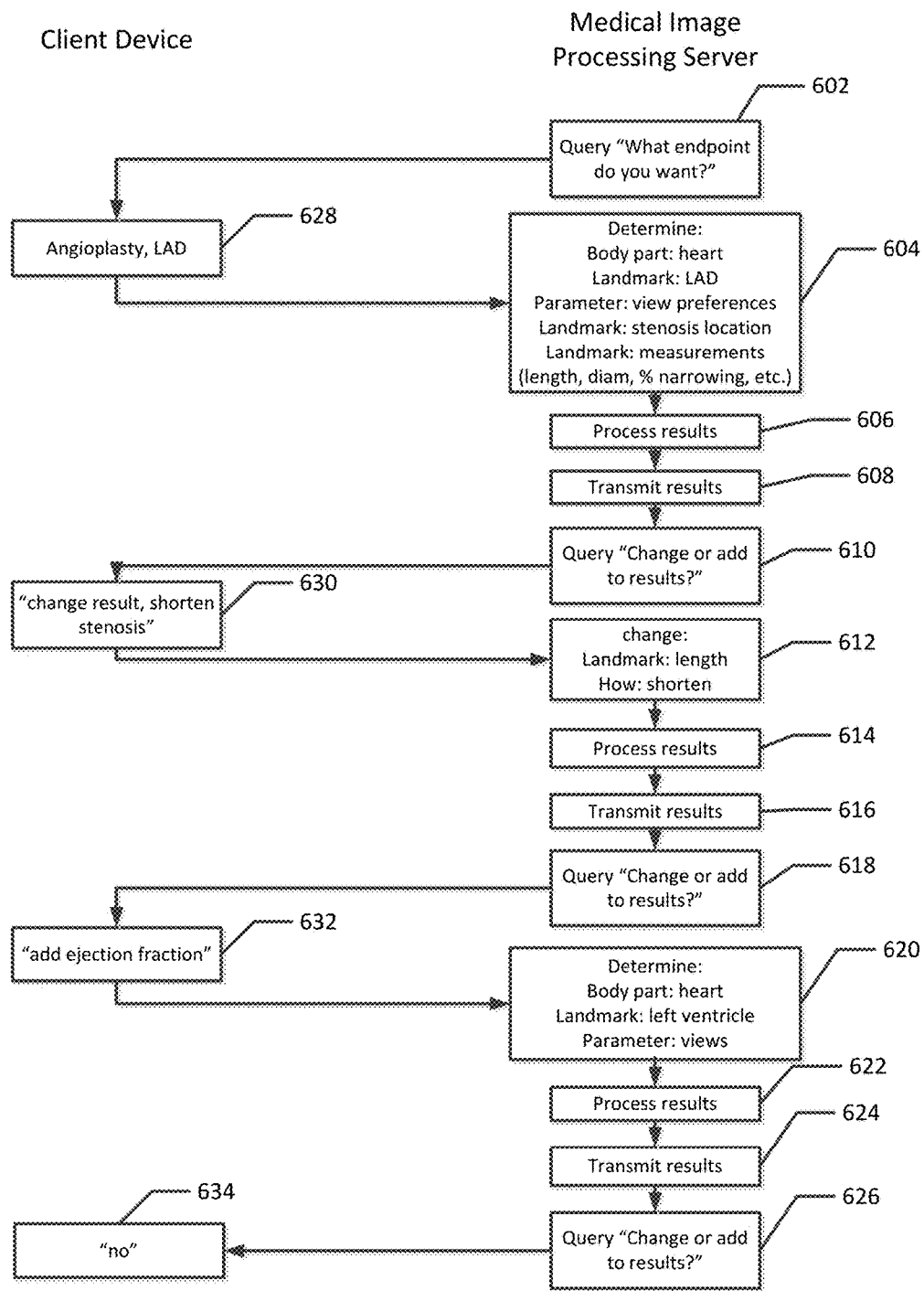
FIG. 6 shows an example of an interactive process between an image processing client and an image processing server according to one embodiment of the invention.

FIG. 6 shows an example of an interactive process between an image processing client and an image processing server according to one embodiment of the invention. Referring to FIG. 6, block 602 represents the initial inquiry by a TAIP system, "what endpoint do you want?" Block 628 represents the user's response, "angioplasty, LAD." Block 604 represents the landmarks and parameters that are used by the TAIP system. Using these anatomical landmarks and parameters, the TAIP system processes the results (block 606) and transmits the results to the client to be displayed therein (block 608). Once the results are displayed, for example, the TAIP queries (e.g., via image processing client) the user whether any additions or changes are desired. Block 630 represents the user's response, "change result" indicating what to change, and "shorten stenosis" indicating how to change it. Block 612 represents the TAIP system's logic in shortening the stenosis length.

It is important to note that there is significant processing logic behind processing the simple command "change result, shorten stenosis". The user has not, in this example, given specific instructions on how much to shorten the stenosis. In this situation, the TAIP system would re-evaluate the outline of the LAD vessel and look for relatively abrupt changes in vessel diameter which are near the previously identified stenosis borders. The system would determine the next most likely border resulting in a shorter stenosis. In this way, the TAIP system can present the user with the most logical result based on a simple voice command.

Other details can be used. For example, the user could have said "change result, shorten stenosis slightly", or "change result, shorten stenosis significantly". In these two examples the TAIP system would find the next logical stenosis border within certain distance parameters. For example, "shorten stenosis slightly" could be interpreted as finding the next most likely stenosis borders which results in an overall stenosis length which is less than, but within 2 millimeters (mm) of, the original stenosis length.

Block 614 and block 616, respectively, represent the processing and transmitting of the altered results. Again, the TAIP system queries the user whether any additions/changes are desired (block 618). In this example, the user wants to add to the result, and block 632 represents his/her voice command of "add ejection fraction." Block 620 represents the landmarks and parameters which the TAIP system determines for this request. The processing and transmitting of the results are represented by blocks 622 and 624, respectively. The user is once again queried for any changes/additions (block 626) and in this example, the user responds "no" (block 634).

Figure 7:
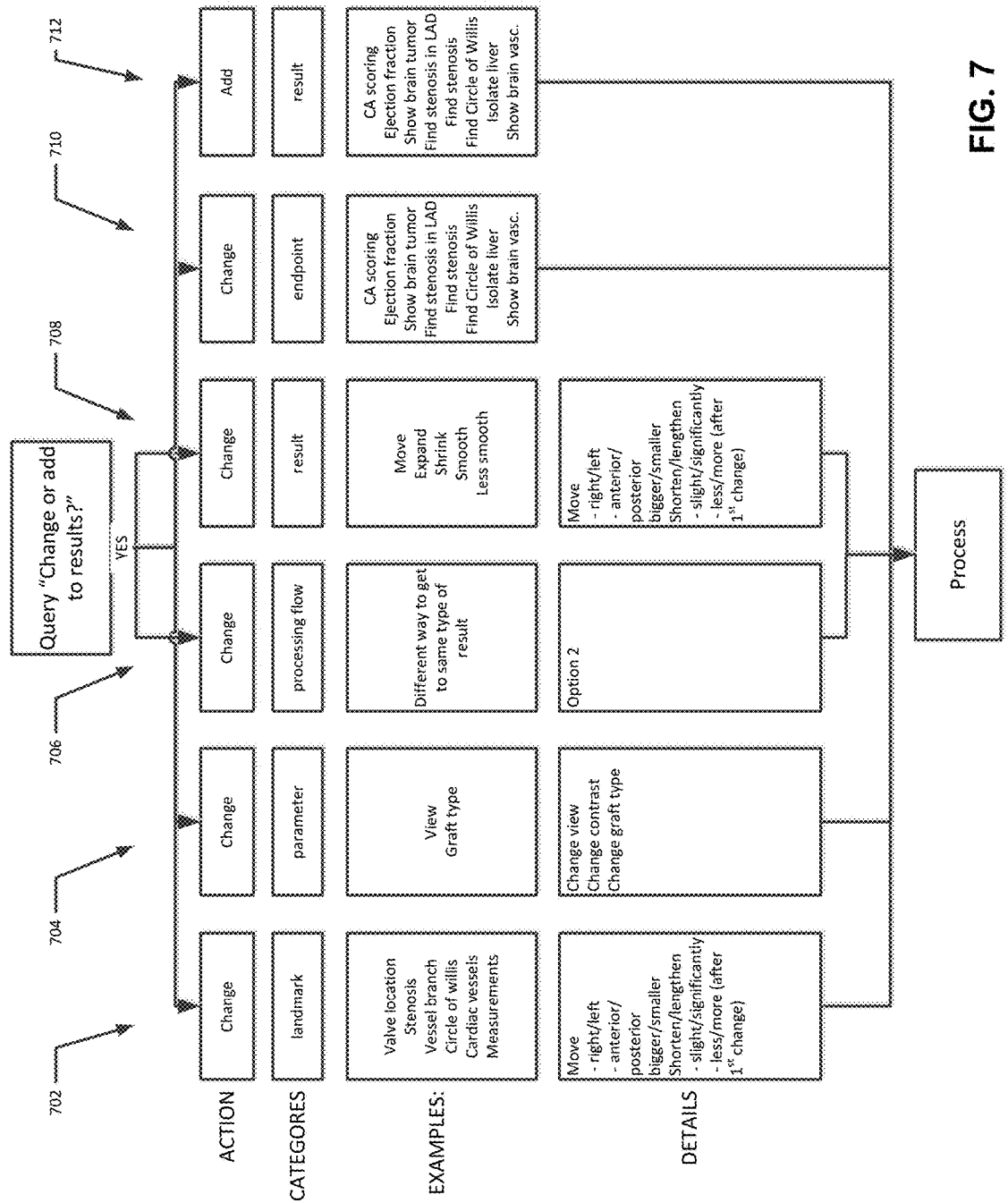
FIG. 7 shows some of the different types of voice commands that the TAIP system can receive and process according to one embodiment of the invention.

FIG. 7 shows some of the different types of voice commands that the TAIP system can receive and process according to one embodiment of the invention. Referring to FIG. 7, this diagram shows some of the commands which will add or change the image processing results. The first row, marked "action" represents the first part of the command, "change" or "add." The second row, marked "categories" includes different categories that can be changed or added, including landmarks, parameters, image processing flow, results and endpoint. The first part of a voice command may include these two items. For example, "change landmark" or "add result." The second part of the voice command may include more details, examples of which are shown in the "details" row. For example, a command might be "change result, shorten stenosis."

Other examples might include: 1) "change landmark, move stenosis down" (which would change the result to a different stenosis than previously shown); 2) "change result, expand tumor" (which would expand the outline, or segmentation, of the featured tumor); 3) "change result, smooth tumor" (which would smooth the outline, or segmentation, of the featured tumor); 4) "change landmark, shorten stenosis, slightly" (which would shorten the identified stenosis, but only slightly, for example, by 1-2 mm or less).

Columns 702, 704, 706, 708, 710, and 712 represent different types of commands which can be performed. Other commands can also be envisioned and this is not meant to be limiting. In addition some of the command types may signal the TAIP system to obtain further feedback from the user. For example, if a user issues the command "move landmark, stenosis," but does not provide the details of how he/she wants to move the stenosis, the TAIP system will display the stenosis, and inquire of the user how he/she wants to move the stenosis. In another example, the user may issue the command "change parameter, graft type," but does not indicate the details of how to change the graft type. The TAIP system would then display the most appropriate options for graft types, possibly showing images and dimensions of the various graft types to help the user decide which one to choose.

Figure 8A:
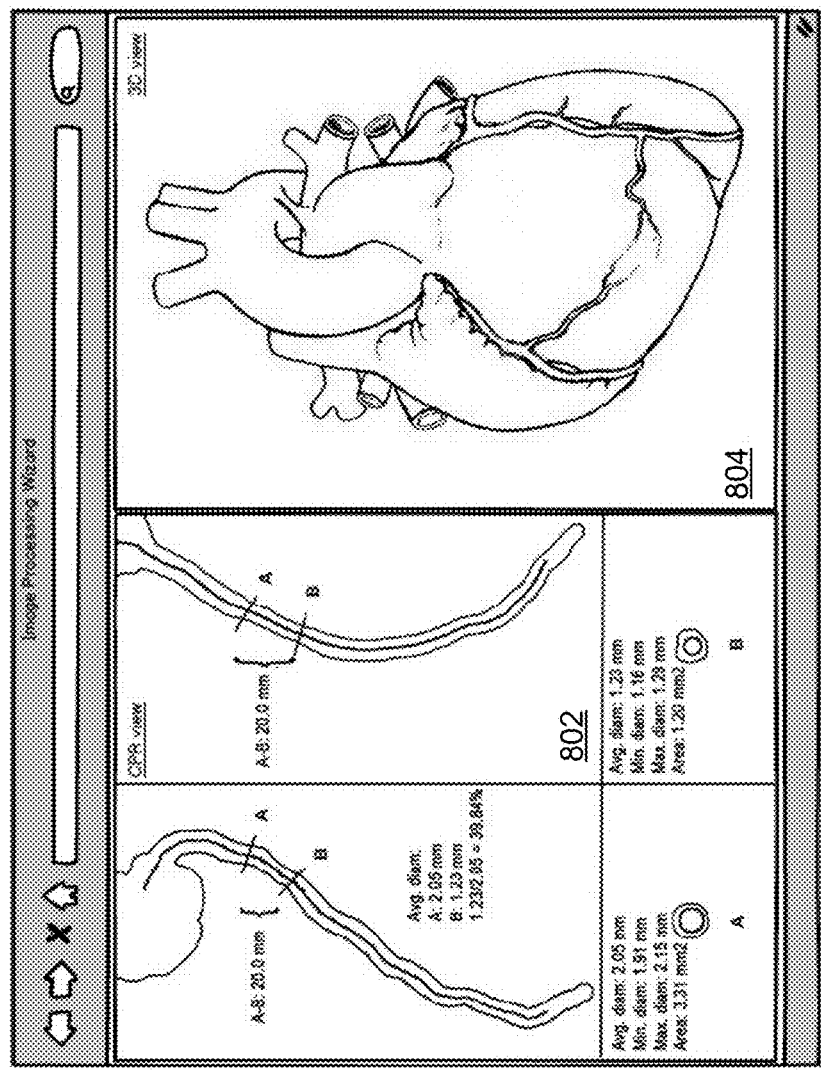
FIGS. 8A-8D are screenshots illustrating examples of graphical user interfaces of an image processing client according to certain embodiments of the invention.

FIGS. 8A-8D are screenshots illustrating examples of graphical user interfaces of an image processing client according to certain embodiments of the invention. FIG. 8A shows an example of what a user might see after issuing a specific command. For example, the user may be performing a cardiovascular angioplasty procedure, or a stent placement procedure, and have issued the verbal command "angioplasty, LAD" or "show stenosis in LAD" or "show LAD" or "show stenosis in heart". In an operating room situation, the TAIP system would have already been loaded with the images relating to the patient in the room. The TAIP system receives the command and using information relating to the patient scan images and also to the user preferences, creates and displays the screen shown in FIG. 8A.

To do this, according to one embodiment, the TAIP system determines several anatomical landmarks and parameters. In general, landmarks are driven by the image data where parameters are driven by the user preferences. For example, a body part landmark represents a heart location and segmentation (determined by the terms "LAD" and/or "stenosis" and/or "heart" and/or "angioplasty"). A landmark can also represents a LAD location and segmentation. The TAIP system can locate the LAD automatically by analyzing the images. This is done by analyzing different tissue densities, edges etc. This analysis may be done in real time or may be performed on the scan images previously to same processing time.) A landmark can also represent a stenosis location and segmentation. Similarly, the TAIP system can determine where there are more sudden changes in the diameter of the LAD, indicating a possible stenosis. A landmark can also represent a vessel dimensions (vessel diameter, length, cross sectional area, volume etc.) or stenosis dimensions (stenosis diameter, length, cross sectional area, volume, % narrowing etc.). A user can specify one or more parameters such as views, where a user may prefer certain views to be displayed for this type of result (cardiac vessel analysis.

Referring back to FIG. 8A, two display areas are shown. Display area 804 shows a 3D view of the heart, with a clear view of the LAD vessel. Display area 802 chows a CPR (curved planar reformation) view of the LAD. Included in the CPR view are detailed measurements including stenosis length, stenosis diameter, minimum and maximum diameters average diameter, and area at different locations along the vessel/stenosis. Also included is percent narrowing of the vessel by the stenosis.

The TAIP system may ask the user if he/she wants any changes. If the answer is a verbal "no," then the display shown in FIG. 8A may remain visible for the duration of the angioplasty procedure to help the physician, and in case changes/additions are wanted further into the procedure. If the physician wants to make changes and/or additions, he/she may respond with a verbal command stating what type of change/addition he/she wants to make. For example, he/she might say "change result, shorten stenosis" if he/she believes the true stenosis may be shorter than what is depicted initially.

Figure 8B:
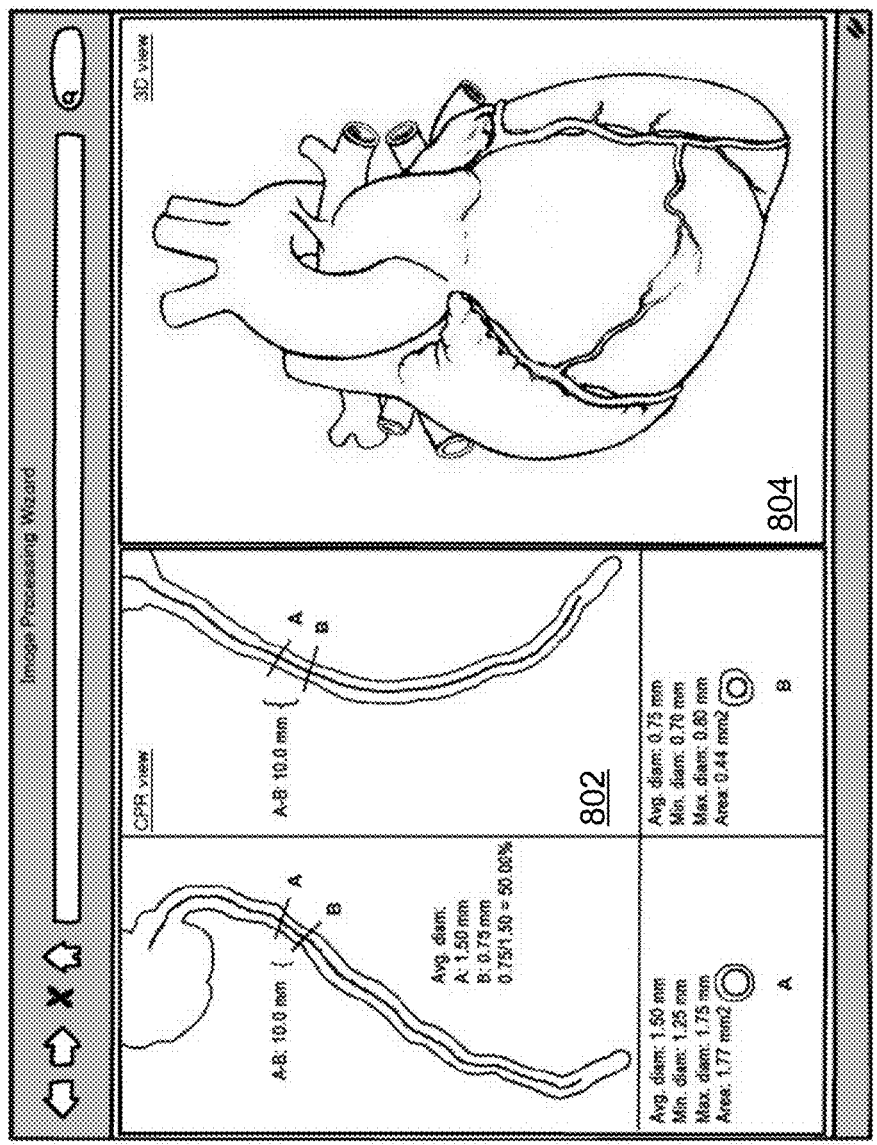

FIG. 8B shows a screen which may be displayed as a result of the "change result, shorten stenosis" command. Note that the stenosis (the area between A and B in the CPR view) is now shorter. Note also that the various measurements, diameters, areas etc., have been recalculated to reflect the changed stenosis length. If the physician is satisfied with these results, he/she may respond "no" when the TAIP system again queries whether any changes/additions are desired. Alternatively, the physician may want some additional information on the patient/condition. For example, the physician may want to see the results of a calcium score, or an ejection fraction analysis. If this is the case, the physician may provide the verbal command "add result, ejection fraction." Again, several landmarks and parameters are used by the TAIP system to automatically generate the results. For example, certain landmarks may be used to identify: 1) heart location and segmentation (determined by the terms "ejection fraction"); 2) right ventricle location and segmentation; 3) areas of calcification; and 4) calcium score (determined by relative area/location of calcified tissue).

Figure 8C:
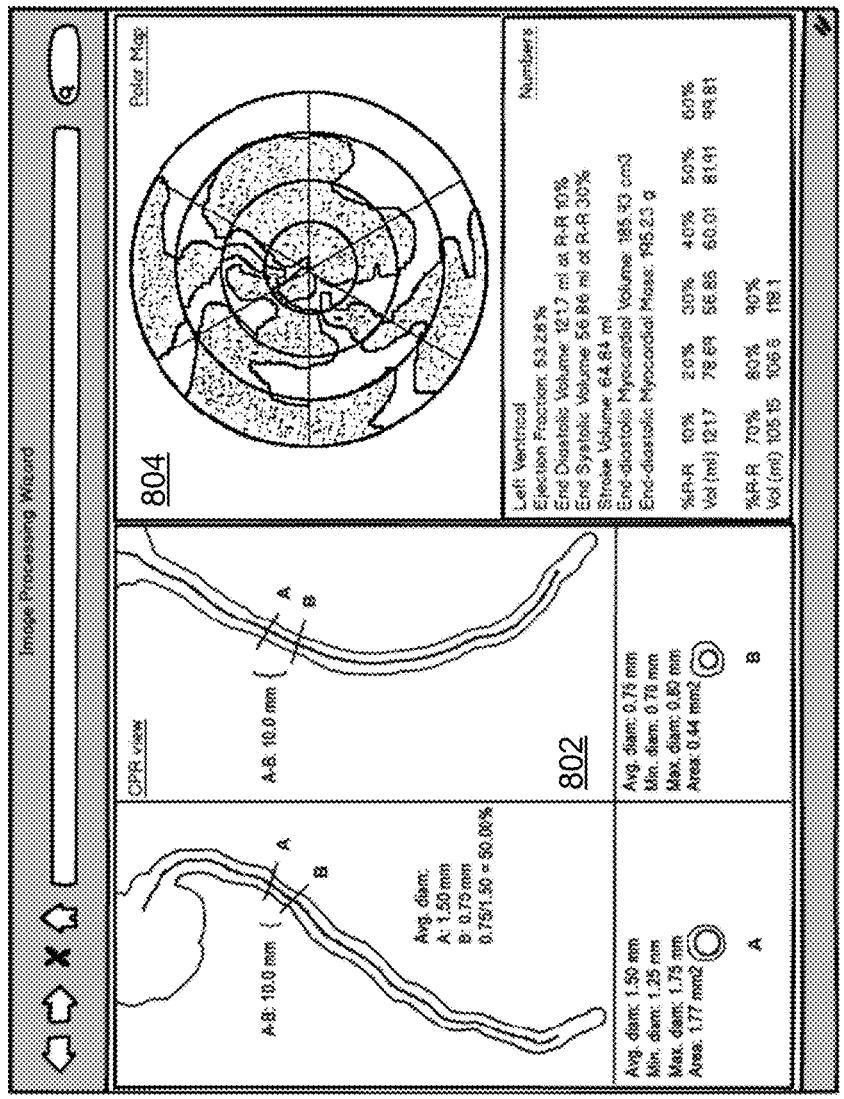

FIG. 8C shows a screen which may be displayed by the TAIP system after a "add result, ejection fraction" command. Note that display area 802 still shows a component of the previous result, the LAD stenosis analysis, while display area 804 now shows the results of the ejection fraction analysis, including a polar map and numerical results. The parameters that include this user's view preferences are used by the TAIP system to create this display. Here the CPR view of the LAD stenosis analysis is shown in display area 802, and the polar map and numbers relating to the ejection fraction analysis are shown in display area 804. However other result views relating to these two analyses are available and may be shown. The parameters dictating this user's view preferences for these two results have determined which result views to show. These preferences may have been manually set by the user previously, or they may be default settings, or they may be the view that the user preferred previously.

Figure 8D:
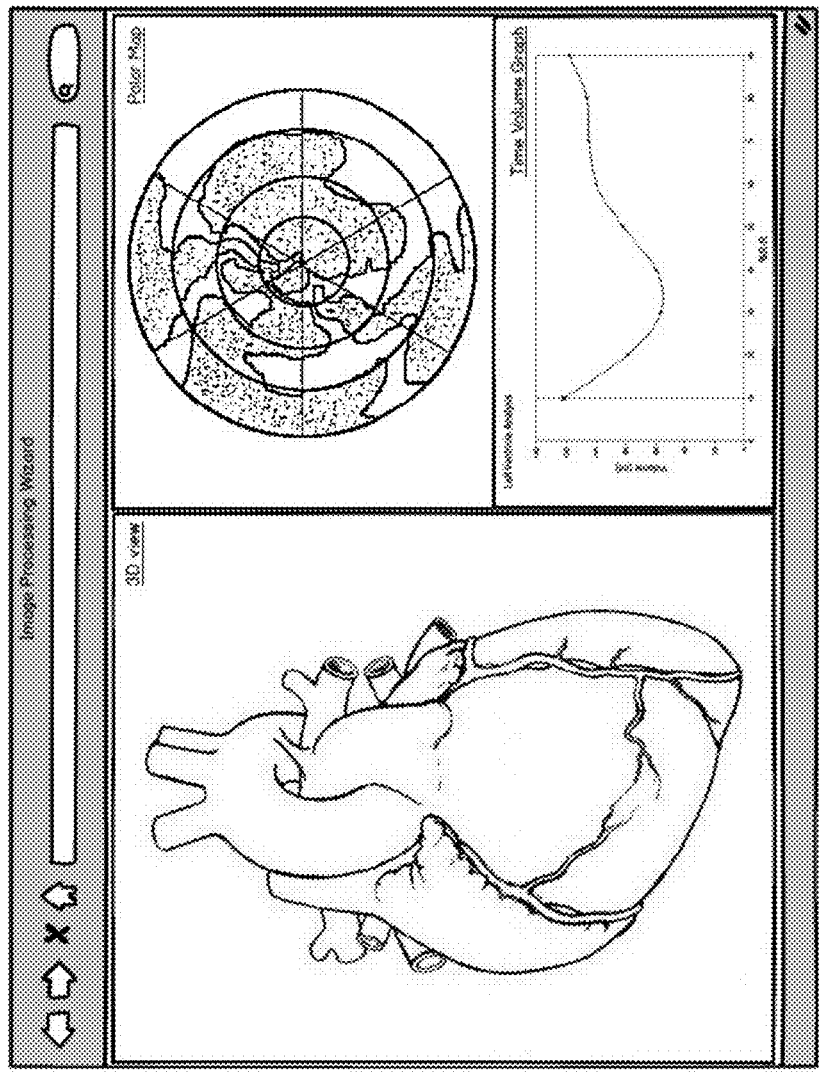

FIG. 8D shows a screen that may be displayed by the TAIP system for a different set of user view preferences. Similar to the screen shown in FIG. 8C, this screen shows the results for a LAD stenosis analysis and an ejection fraction analysis. However, the views are very different. This user has view preferences which prioritize the 3D LAD view over the CPR LAD view. Also, this user prefers to see a time volume graph rather than the ejection fraction numbers results shown in FIG. 8C. Again, the TAIP system will query whether any changes/additions are desired. If the physician wants changes to any parameters or landmarks, he/she would provide a verbal command identifying the specific changes/additions.

In this way, the TAIP system can provide precisely the views and results that the user requires with a minimum of commands. Since providing touchless commands can be cumbersome, keeping complexity and number of commands to a minimum, allows the user to focus on the sterile procedure at hand. TAIP can also take advantage of pre-built workflow elements. For example, in EVAR (Endo-vascular aneurysm repair) procedure, surgeons need to look the front- and back-views of abdominal aorta, left and right renal arteries and iliac arteries. TAIP system can be set up to pre-build these views, and allows easy "next" and "previous" or similar commands or motion to further simplify the navigation in commands, gestures or devices used.

Figure 9A:
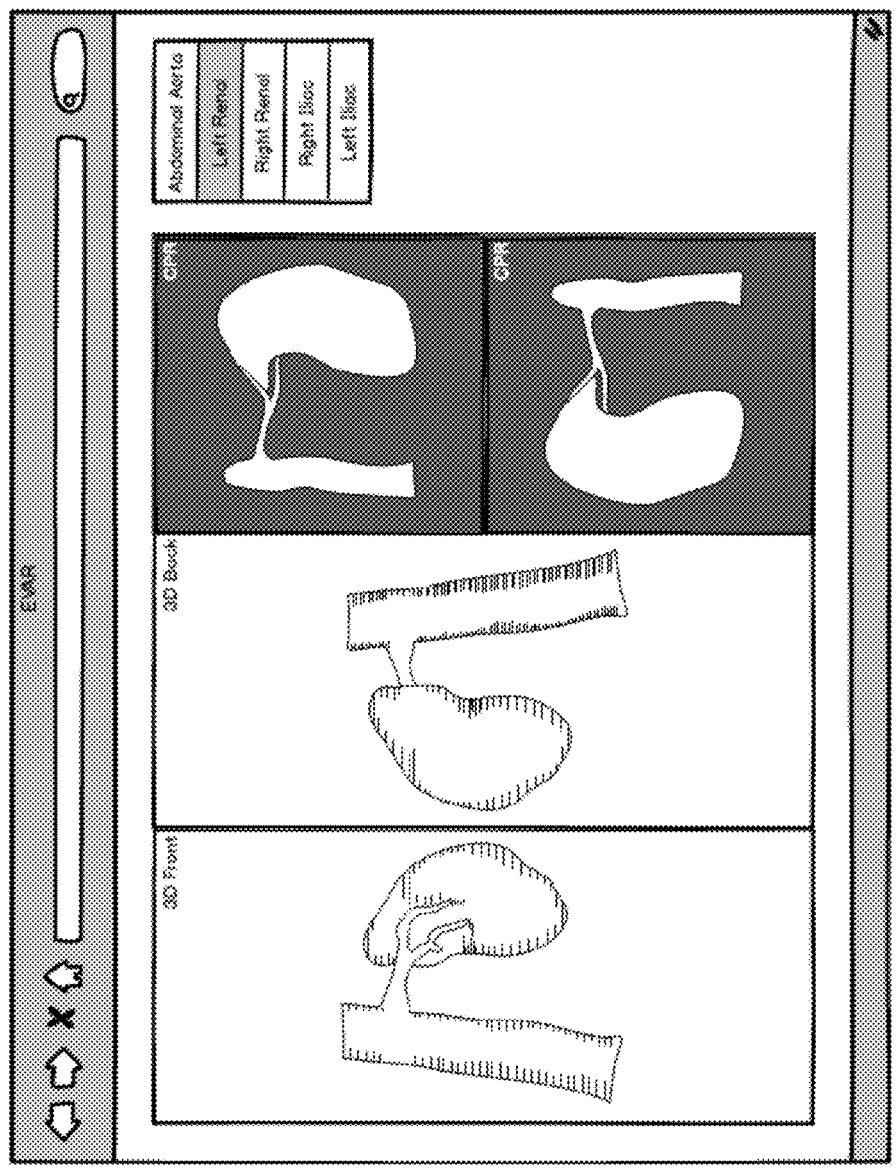
FIGS. 9A-9D are screenshots illustrating examples of graphical user interfaces of an image processing client according to alternative embodiments of the invention.
Figure 9B:
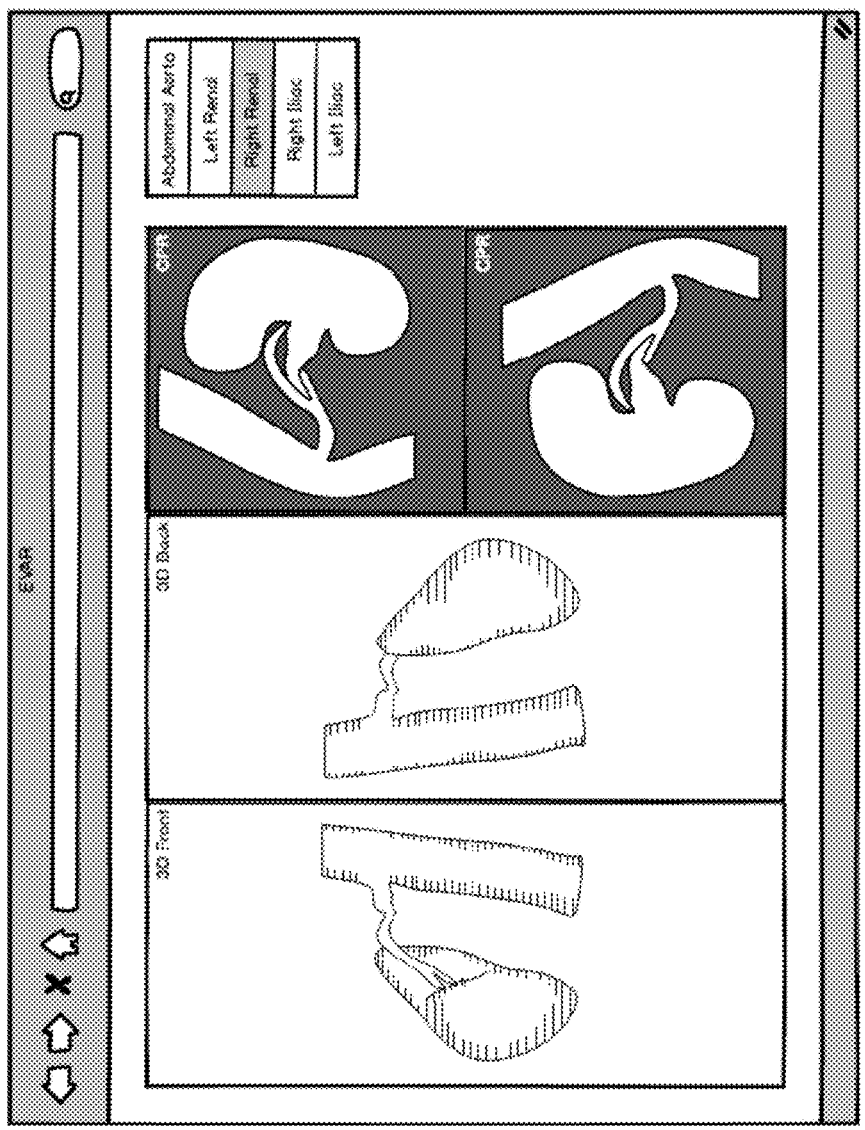
Figure 9C:
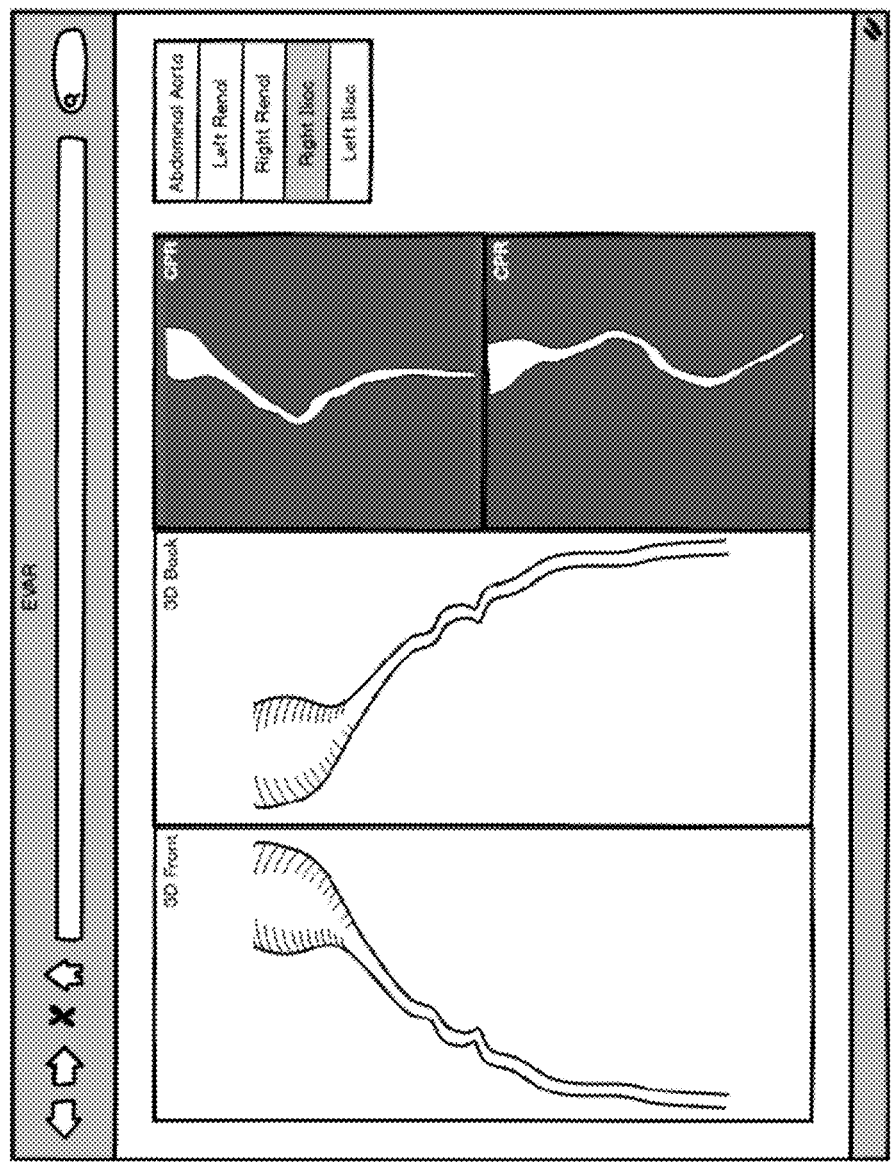
Figure 9D:
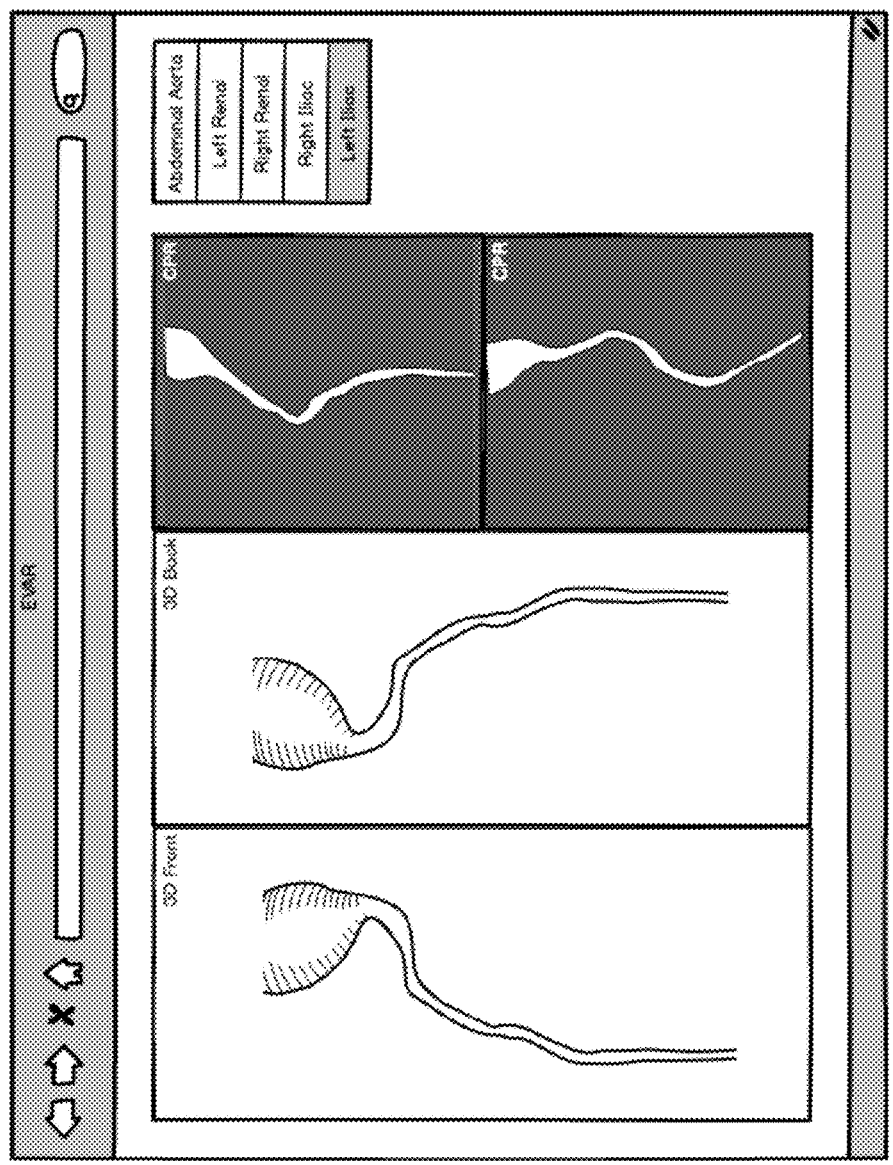

FIGS. 9A-9D show various example screenshots of pre-built workflows according to certain embodiments of the invention. FIG. 9A is a screen showing detailed views of the left renal artery. The views include 3D front, 3D back and CPR (Curved Planar Reformatted) views. This screen may be viewed by issuing the voice command "left renal" or "next" or "previous". FIG. 9B is a screen showing detailed views of the right renal artery. The views include 3D front, 3D back and CPR (Curved Planar Reformatted) views. This screen may be viewed by issuing the voice command "right renal" or "next" or "previous." FIG. 9C is a screen showing detailed views of the right iliac artery. The views include 3D front, 3D back and CPR (Curved Planar Reformatted) views. This screen may be viewed by issuing the voice command "right iliac" or "next" or "previous." FIG. 9D is a screen showing detailed views of the left iliac artery. The views include 3D front, 3D back and CPR (Curved Planar Reformatted) views. This screen may be viewed by issuing the voice command "left iliac" or "next" or "previous."

As described above, a variety of image processing tools can be accessed by used by image processing engine 120 and/or image processing systems 105 of FIG. 1. The following are examples of medical image processing tools that may be included as part of the image processing system described above. These examples are provided for illustrative purposes and not intended to be a limitation of the present invention.

Vessel analysis tools may include a comprehensive vascular analysis package for CT and MR angiography capable of a broad range of vascular analysis tasks, from coronary arteries to aortic endograft planning and more general vascular review, including carotid and renal arteries. Auto-centerline extraction, straightened view, diameter and length measurements, CPR and axial renderings, and Vessel Track mode for automated thin-slab MIP may be included.

Calcium scoring tools may include Semi-automated identification of coronary calcium with Agatston, volume and mineral mass algorithms. An integrated reporting package with customization options may be included.

Time-dependent analysis tools may include time-resolved planar or volumetric 4D brain perfusion examinations acquired with CT or MR. The TDA tools may support color or mapping of various parameters such as mean enhancement time and enhancement integral, with semi-automated selection of input function and baseline, to speed analysis. TDA tools may support rapid automated processing of dynamic 4D area-detector CT examinations to ensure interpretation within minutes of acquisition.

CT/CTA (Computed tomography angiography) subtraction tools are used in the removal of non-enhancing structures (e.g. bone) from CT angiography examinations, the CT/CTA option includes automatic registration of pre- and post-contrast images, followed by a dense-voxel masking algorithm which removes high-intensity structures (like bone and surgical clips) from the CTA scan without increasing noise, aiding with the isolation of contrast-enhanced vascular structures.

Lobular decomposition tools identify tree-like structures within a volume of interest, e.g. a scan region containing a vascular bed, or an organ such as the liver. The LD tool can then identifies sub-volumes of interest based on proximity to a given branch of the tree or one of its sub-branches. Research applications include the analysis of the lobular structure of organs.

General Enhancement & Noise Treatment with Low Exposure tools may include an advanced volumetric filter architecture applying noise management techniques to improve the effectiveness of 3D, centerline, contouring and segmentation algorithms even when source image quality is not optimum.

The Spherefinder tools perform automated analysis of volumetric examinations to identify the location of structures with a high sphericity index (characteristics exhibited by many nodules and polyps). Spherefinder is often used with Lung or Colon CT scans to identify potential areas of interest.

Segmentation, analysis & tracking tools support analysis and characterization of masses and structures, such as solitary pulmonary nodules or other potential lesions. Tools may identify and segment regions of interest, and then apply measurement criteria, such as RECIST and WHO, leading to tabulated reporting of findings and follow-up comparison. Display and management of candidate markers from optional detection engines may be supported, including Spherefinder.

Time volume analysis tools may provide automated calculation of ejection fraction from a chamber in rhythmic motion, such as a cardiac ventricle. A fast and efficient workflow may be included to enable the user to identify the wall boundaries of interest (e.g. epicardium and endocardium) and, based on these user-confirmed regions of interest, to report ejection fraction, wall volume (mass) and wall thickening from multi-phasic CT data. Tabulated reporting output is included.

Maxillo-facial tools support the analysis and visualization of CT examinations of the Maxillo-facial region, these tools apply the CPR tool to generate "panoramic" projections in various planes and of various thicknesses, and cross-sectional MPR views at set increments along the defined curve plane.

Applicable to endoluminal CT or MR investigations such as colon, lungs, or blood vessels, the Flythrough tools supports side-by-side review, painting of previously-viewed areas, percent coverage tracking, and multiple screen layouts including forward, reverse, fisheye and flat volume rendered views. Tools for contrast subtraction, "Cube View", and integrated contextual reporting may be supported. Display and management of candidate markers from optional detection engines may be supported, including iNtuition's Spherefinder.

The Volumetric Histogram tools allow a volume of interest to be segmented and analyzed for composition. Research applications include the analysis of low-attenuation regions of the lungs, threshold-based division of tumors into voxel populations, investigation of thrombosed vessels or aneurysms, or other pathology.

Findings workflow tools provide a framework for tracking findings across serial examinations. A database holds measurements and key images, and provides support for structured comparisons and tabulated reporting of findings over time, such as the RECIST 1.1 approach for presenting serial comparisons. The Annotation and Image Markup (AIM) XML schema may be supported, for automated integration with voice-recognition systems or clinical databases, and Word-based reports may be derived from the database.

With these tools, any two CT, PET, MR or SPECT series, or any two-series combination thereof can be overlaid with one assigned a semi-transparent color coding and the other shown in grayscale and volume rendering for anatomical reference. Automatic registration is provided and subtraction to a temporary series or to a saved, third series is possible. Support for PET/MR visualization is included.

Certain MR examinations (for example, Breast MR) involve a series of image acquisitions taken over a period of time, where certain structures become enhanced over time relative to other structures. These tools feature the ability to subtract a pre-enhancement image from all post-enhancement images to emphasize visualization of enhancing structures (for example, vascular structures and other enhancing tissue). Time-dependent region-of-interest tools may be provided to plot time-intensity graphs of a given region.

Parametric mapping tools are an enhancement to the Multi-Phase MR tools, the parametric mapping option pre-calculates overlay maps where each pixel in an image is color-coded depending on the time-dependent behavior of the pixel intensity. As an example, this tool can be used in Breast MR to speed identification and investigation of enhancing regions.

The MultiKv tools provide support for Dual Energy and Spectral Imaging acquisitions from multiple vendors, providing standard image processing algorithms such as segmentation or contrast suppression, as well as generic toolkits for precise analysis and development of new techniques.

The embodiments described above can be applied to a variety of medical areas. For example, the techniques described above can be applied to vessel analysis (including Endovascular Aortic Repair (EVAR) and electrophysiology (EP) planning). Such vessel analysis is performed for interpretation of both coronary and general vessel analysis such as carotid and renal arteries, in addition to aortic endograft and electro-physiology planning. Tools provided as cloud services include auto-centerline extraction, straightened view, diameter and length measurements, Curved Planar Reformation (CPR) and axial renderings, as well as charting of the vessel diameter vs. distance and cross-sectional views. The vessel track tool provides a Maximum Intensity Projection (MIP) view in two orthogonal planes that travels along and rotates about the vessel centerline for ease of navigation and deep interrogation. Plaque analysis tools provide detailed delineation of non luminal structure such as soft plaque, calcified plaque and intra-mural lesions.

In addition, the techniques described above can be utilized in the area of endovascular aortic repair. According to some embodiments, vascular analysis tools provided as cloud services support definition of report templates which captures measurements for endograft sizing. Multiple centerlines can be extracted to allow for planning of EVAR procedures with multiple access points. Diameters perpendicular to the vessel may be measured along with distances along the two aorto-iliac paths. Custom workflow templates may be used to enable the major aortic endograft manufactures' measurement specifications to be made as required for stent sizing. Sac segmentation and volume determination with a "clock-face" overlay to aid with documenting the orientation and location of branch vessels for fenestrated and branch device planning, may also be used. Reports containing required measurements and data may be generated.

The techniques described above can also be applied in the left atrium analysis mode, in which semi-automated left atrium segmentation of each pulmonary vein ostium is supported with a single-click distance pair tool, provided as cloud services, for assessment of the major and minor vein diameter. Measurements are automatically detected and captured into the integrated reporting system. These capabilities can be combined with other vessel analysis tools to provide a comprehensive and customized EP planning workflow for ablation and lead approach planning.

The techniques described above can also be utilized in calcium scoring. Semi-automated identification of coronary calcium is supported with Agatston, volume and mineral mass algorithms being totaled and reported on-screen. Results may be stored in an open-format database along with various other data relating to the patient and their cardiovascular history and risk factors. A customized report can be automatically generated, as part of cloud services, based upon these data. Also includes report generation as defined by the Society of Cardiovascular Computed Tomography (SCCT) guidelines.

The techniques described above can also be utilized in a time-volume analysis (TVA), which may include fully-automated calculation of left ventricular volume, ejection fraction, myocardial volume (mass) and wall thickening from multi-phasic data. A fast and efficient workflow provided as part of cloud services allows for easy verification or adjustment of levels and contours. The results are presented within the integrated reporting function.

The techniques described above can also be utilized in the area of segmentation analysis and tracking (SAT), which includes supports analysis and characterization of masses and structures in various scans, including pulmonary CT examinations. Features include single-click segmentation of masses, manual editing tools to resolve segmentation issues, automatic reporting of dimensions and volume, graphical 3D display of selected regions, integrated automated reporting tool, support for follow-up comparisons including percent volume change and doubling time, and support for review of sphericity filter results.

The techniques described above can also be utilized in the area of flythrough which may include features of automatic segmentation and centerline extraction of the colon, with editing tools available to redefine these centerlines if necessary. 2D review includes side-by-side synchronized supine and prone data sets in either axial, coronal or sagittal views with representative synchronized endoluminal views. 3D review includes axial, coronal and sagittal MPR or MIP image display with large endoluminal view and an unfolded view that displays the entire colon. Coverage tracking is supported to ensure 100% coverage with stepwise review of unviewed sections, one-click polyp identification, bookmark and merge findings, as well as a cube view for isolating a volume of interest and an integrated contextual reporting tool. Support is provided for use of sphericity filter results.

The techniques described above can also be utilized in the area of time-dependent analysis (TDA), which provides assessment tools for analyzing the time-dependent behavior of appropriate computerized tomographic angiography (CTA) and/or MRI examinations, such as within cerebral perfusion studies. Features include support for loading multiple time-dependent series at the same time, and a procedural workflow for selecting input and output function and regions of interest. An integrated reporting tool is provided as well as the ability to export the blood flow, blood volume and transit time maps to DICOM. The tools may also be used with time-dependent MR acquisitions to calculate various time-dependent parameters.

The techniques described above can also be utilized in the area of CTA-CT subtraction, which includes automatic registration of pre- and post-contrast images, followed by subtraction or dense-voxel masking technique which removes high-intensity structures (like bone and surgical clips) from the CTA scan without increasing noise, and leaving contrast-enhanced vascular structures intact.

The techniques described above can also be utilized in dental analysis, which provides a CPR tool which can be applied for review of dental CT scans, offering the ability to generate "panoramic" projections in various planes and of various thicknesses, and cross-sectional MPR views at set increments along the defined curve plane.

The techniques described above can also be utilized in the area of multi-phase MR (basic, e.g. breast, prostate MR). Certain MR examinations (for example, breast, prostate MR) involve a series of image acquisitions taken over a period of time, where certain structures become enhanced over time relative to other structures. This module features the ability to subtract a pre-enhancement image from all post-enhancement images to emphasize visualization of enhancing structures (for example, vascular structures and other enhancing tissue). Time-dependent region-of-interest tools are provided to plot time-intensity graphs of a given region.

The techniques described above can also be utilized in parametric mapping (e.g. for multi-phase Breast MR), in which the parametric mapping module pre-calculates overlay maps where each pixel in an image is color-coded depending on the time-dependent behavior of the pixel intensity. The techniques described above can also be utilized in the area of SphereFinder (e.g. sphericity filter for lung and colon). SphereFinder pre-processes datasets as soon as they are received and applies filters to detect sphere-like structures. This is often used with lung or colon CT scans to identify potential areas of interest. The techniques described can also be utilized in fusion for CT/MR/PET/SPECT. Any two CT, PET, MR or SPECT series, or any two-series combination can be overlaid with one assigned a semi-transparent color coding and the other shown in grayscale and volume rendering for anatomical reference. Automatic registration is provided and subtraction to a temporary series or to a saved, third series is possible.

The techniques described above can also be utilized in the area of Lobular Decomposition. Lobular Decomposition is an analysis and segmentation tool that is designed with anatomical structures in mind. For any structure or organ region which is intertwined with a tree-like structure (such as an arterial and/or venous tree), the Lobular Decomposition tool allows the user to select the volume of interest, as well as the trees related to it, and to partition the volume into lobes or territories which are most proximal to the tree or any specific sub-branch thereof. This generic and flexible tool has potential research applications in analysis of the liver, lung, heart and various other organs and pathological structures.

The techniques described above can also be utilized in the area of Volumetric Histogram. Volumetric Histogram supports analysis of a given volume of interest based on partition of the constituent voxels into populations of different intensity or density ranges. This can be used, for example, to support research into disease processes such as cancer (where it is desirable to analyze the composition of tumors, in an attempt to understand the balance between active tumor, necrotic tissue, and edema), or emphysema (where the population of low-attenuation voxels in a lung CT examination may be a meaningful indicator of early disease).

The techniques described above can also be utilized in the area of Motion Analytics. Motion Analytics provides a powerful 2D representation of a 4D process, for more effective communication of findings when interactive 3D or 4D display is not available. Any dynamic volume acquisition, such as a beating heart, can be subjected to the Motion Analysis, to generate a color-coded "trail" of outlines of key boundaries, throughout the dynamic sequence, allowing a single 2D frame to capture and illustrate the motion, in a manner that can be readily reported in literature. The uniformity of the color pattern, or lack thereof, reflects the extent to which motion is harmonic, providing immediate visual feedback from a single image.

Figure 10:
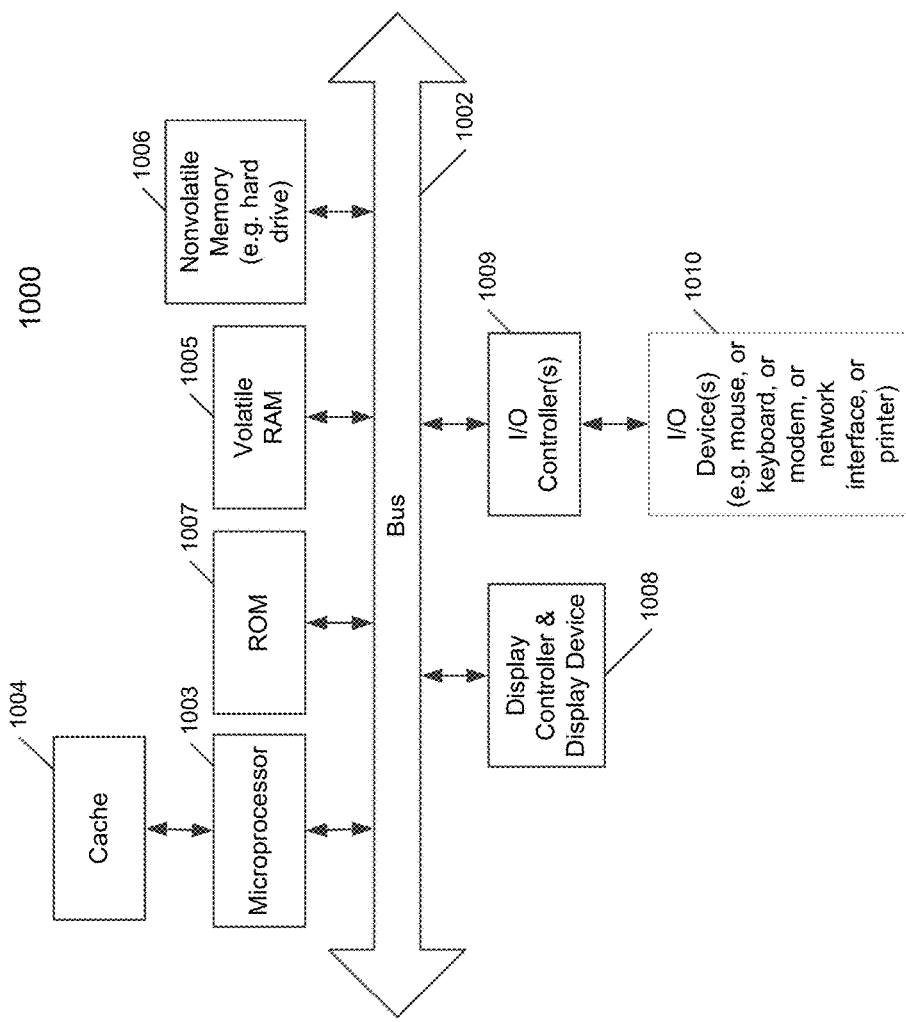
FIG. 10 is a block diagram of a data processing system, which may be used with one embodiment of the invention.

FIG. 10 is a block diagram of a data processing system, which may be used with one embodiment of the invention. For example, the system 1000 may be used as part of a server or a client as described above. For example, system 1000 may represent any of the client devices (e.g., client devices 101-102) or image processing server (e.g., server 104) described above. Note that while FIG. 10 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used with the present invention.

As shown in FIG. 10, the computer system 1000, which is a form of a data processing system, includes a bus or interconnect 1002 which is coupled to one or more microprocessors 1003 and a ROM 1007, a volatile RAM 1005, and a non-volatile memory 1006. The microprocessor 1003 is coupled to cache memory 1004. The bus 1002 interconnects these various components together and also interconnects these components 1003, 1007, 1005, and 1006 to a display controller and display device 1008, as well as to input/output (I/O) devices 1010, which may be mice, keyboards, modems, network interfaces, printers, and other devices which are well-known in the art.

Typically, the input/output devices 1010 are coupled to the system through input/output controllers 1009. The volatile RAM 1005 is typically implemented as dynamic RAM (DRAM) which requires power continuously in order to refresh or maintain the data in the memory. The non-volatile memory 1006 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 10 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1002 may include one or more buses connected to each other through various bridges, controllers, and/or adapters, as is well-known in the art. In one embodiment, the I/O controller 1009 includes a USB (Universal Serial Bus) adapter for controlling USB peripherals. Alternatively, I/O controller 1009 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A computer-implemented method for medical image processing, the method comprising:
    displaying a first medical image at a display device of a client device, wherein the first medical image was received from an image processing server over a network;
    receiving, by a gesture control module hosted by the client device, a signal from one or more sensors;
    determining, by the gesture control module, a user action of a user based on the signal, the user action representing a physical action of the user;
    determining, by a command processing module, whether the user action is valid in view of the first medical image, including
        performing a lookup operation in an action data structure to determine whether the user action is listed in the action data structure, and
        in response to determining that the user action is not listed in the action data structure, presenting a message to the user indicating that the user action is invalid;
    in response to determining that the user action is valid, transmitting a request to the image processing server over the network, the request including a user action identifier (ID) identifying the user action and an optional image ID identifying the first medical image;
    receiving a second medical image from the image processing server, wherein the second medical image was generated by the image processing server by performing one or more image processing operations that were determined based on the user action ID and the image ID of the first medical image; and
    displaying the second medical image at the display device of the client device.

2. The method of claim 1, wherein the image processing operation comprises performing a measurement based on one or more landmarks of the first medical image, and wherein the second medical image represents a result of the measurement based on the first medical image.

3. The method of claim 1, wherein the one or more sensors comprise at least one of a microphone, a camera, an infrared sensor, or a motion detector, and wherein the user action was performed without physically touching the client device.

4. The method of claim 1, wherein the request further comprises one or more landmarks associated with the first medical image currently displayed at the client device.

5. The method of claim 1, wherein the action data structure contains a list of predetermined actions that have been configured as valid for the first medical image.

6. The method of claim 1, wherein the image processing server is configured to determine one or more image processing commands based on the user action ID, including
    performing a lookup operation in an action to command (action/command) mapping data structure based on one or more landmarks of the first medical image to identify a first set of one or more image processing commands; and
    determining a second set of one or more image processing commands from the first set based on the user action ID.

7. A non-transitory machine-readable medium having instructions stored therein, which when executed by a processor, cause the processor to perform a method for medical image processing, the method comprising:
    displaying a first medical image at a display device of a client device, wherein the first medical image was received from an image processing server over a network;
    receiving, by a gesture control module hosted by the client device, a signal from one or more sensors;
    determining, by the gesture control module, a user action of a user based on the signal, the user action representing a physical action of the user;
    determining, by a command processing module, whether the user action is valid in view of the first medical image, including
        performing a lookup operation in an action data structure to determine whether the user action is listed in the action data structure, and
        in response to determining that the user action is not listed in the action data structure, presenting a message to the user indicating that the user action is invalid;
    in response to determining that the user action is valid, transmitting a request to the image processing server over the network, the request including a user action identifier (ID) identifying the user action and an optional image ID identifying the first medical image;
    receiving a second medical image from the image processing server, wherein the second medical image was generated by the image processing server by performing one or more image processing operations that were determined based on the user action ID and the image ID of the first medical image; and
    displaying the second medical image at the display device of the client device.

8. The machine-readable medium of claim 7, wherein the image processing operation comprises performing a measurement based on one or more landmarks of the first medical image, and wherein the second medical image represents a result of the measurement based on the first medical image.

9. The machine-readable medium of claim 7, wherein the one or more sensors comprise at least one of a microphone, a camera, an infrared sensor, or a motion detector, and wherein the user action was performed without physically touching the client device.

10. The machine-readable medium of claim 7, wherein the request further comprises one or more landmarks associated with the first medical image currently displayed at the client device.

11. The machine-readable medium of claim 7, wherein the action data structure contains a list of predetermined actions that have been configured as valid for the first medical image.

12. The machine-readable medium of claim 7, wherein the image processing server is configured to determine one or more image processing commands based on the user action ID, including
performing a lookup operation in an action to command (action/command) mapping data structure based on one or more landmarks of the first medical image to identify a first set of one or more image processing commands; and
determining a second set of one or more image processing commands from the first set based on the user action ID.

13. A data processing system, comprising:
a processor; and
a memory coupled to the processor to store instructions, which when executed by the processor, cause the processor to perform a method, the method including
displaying a first medical image at a display device of a client device, wherein the first medical image was received from an image processing server over a network,
receiving, by a gesture control module hosted by the client device, a signal from one or more sensors,
determining, by the gesture control module, a user action of a user based on the signal, the user action representing a physical action of the user, including
performing a lookup operation in an action data structure to determine whether the user action is listed in the action data structure, and
in response to determining that the user action is not listed in the action data structure, presenting a message to the user indicating that the user action is invalid,
determining, by a command processing module, whether the user action is valid in view of the first medical image,
in response to determining that the user action is valid, transmitting a request to the image processing server over the network, the request including a user action identifier (ID) identifying the user action and an optional image ID identifying the first medical image,
receiving a second medical image from the image processing server, wherein the second medical image was generated by the image processing server by performing one or more image processing operations that were determined based on the user action ID and the image ID of the first medical image, and
displaying the second medical image at the display device of the client device.

14. The system of claim 13, wherein the image processing operation comprises performing a measurement based on one or more landmarks of the first medical image, and wherein the second medical image represents a result of the measurement based on the first medical image.

15. The system of claim 13, wherein the one or more sensors comprise at least one of a microphone, a camera, an infrared sensor, or a motion detector, and wherein the user action was performed without physically touching the client device.

16. The system of claim 13, wherein the request further comprises one or more landmarks associated with the first medical image currently displayed at the client device.

17. The system of claim 13, wherein the action data structure contains a list of predetermined actions that have been configured as valid for the first medical image.

* * * * *